(12) United States Patent
Zavattari et al.

(10) Patent No.: US 12,195,809 B2
(45) Date of Patent: Jan. 14, 2025

(54) METHOD FOR THE DIAGNOSIS AND/OR PROGNOSIS OF CANCER OF THE BILIARY TRACT

(71) Applicant: UNIVERSITÀ DEGLI STUDI DI CAGLIARI, Cagliari (IT)

(72) Inventors: Patrizia Zavattari, Cagliari (IT); Mario Scartozzi, Cagliari (IT); Eleonora Loi, Cagliari (IT); Cesare Zavattari, Cagliari (IT); Alessandro Tommasi, Cagliari (IT); Sergio Alonso, Cagliari (IT); Andrea Casadei Gardini, Cagliari (IT); Matías A. Avila, Cagliari (IT)

(73) Assignee: UNIVERSITÀ DEGLI STUDI DI CAGLIARI, Cagliari (IT)

( * ) Notice: Subject to any disclaimer, the term of this patent is extended or adjusted under 35 U.S.C. 154(b) by 0 days.

(21) Appl. No.: 18/681,524

(22) PCT Filed: Aug. 3, 2022

(86) PCT No.: PCT/IB2022/057191
§ 371 (c)(1),
(2) Date: Feb. 6, 2024

(87) PCT Pub. No.: WO2023/012683
PCT Pub. Date: Feb. 9, 2023

(65) Prior Publication Data
US 2024/0263249 A1    Aug. 8, 2024

(30) Foreign Application Priority Data
Aug. 6, 2021    (IT) .................. 102021000021455

(51) Int. Cl.
*C12Q 1/6886* (2018.01)
(52) U.S. Cl.
CPC ..... *C12Q 1/6886* (2013.01); *C12Q 2600/154* (2013.01)
(58) Field of Classification Search
CPC .................... C12Q 1/6886; C12Q 2600/154
See application file for complete search history.

(56) References Cited

U.S. PATENT DOCUMENTS

2016/0090634 A1    3/2016   Kisiel et al.

FOREIGN PATENT DOCUMENTS

| CN | 107727865 A | 2/2018 | |
|---|---|---|---|
| KR | 20140095040 A | 7/2014 | |
| WO | 2010007083 A2 | 1/2010 | |
| WO | WO2020/069350 A1 * | 4/2020 | ............. C12N 15/10 |
| WO | 2020163410 A1 | 8/2020 | |
| WO | 2020240031 A1 | 12/2020 | |

OTHER PUBLICATIONS

Yi Shu, et al., Identification of methylation profile of HOX genes in extrahepatic cholangiocarcinoma, World Journal of Gastroenterology, 2011, pp. 3407-3419, vol. 17 No. 29.
Annika Bergquist, et al., Epidemiology of cholangiocarcinoma, Best Practice & Research Clinical Gastroenterology, 2015, pp. 221-232, vol. 29.
Davendra P.S. Sohal, et al., Molecular characteristics of biliary tract cancer, Critical Reviews in Oncology Hematology, 2016, pp. 111-118, vol. 107.
Sarinya Kongpetch, et al., Pathogenesis of cholangiocarcinoma: From genetics to signalling pathways, Best Practice & Research Clinical Gastroenterology, 2015, pp. 233-244, vol. 29.
Kirsten Boonstra, et al., Population-Based Epidemiology, Malignancy Risk, and Outcome of Primary Sclerosing Cholangitis, Hepatology, 2013, pp. 2045-2055, vol. 58 No. 6.
Sumera Rizvi, et al., Primary Sclerosing Cholangitis as a Premalignant Biliary Tract Disease: Surveillance and Management, Clinical Gastroenterology and Hepatology, 2015, pp. 2152-2165, vol. 13 No. 12.
Murad Aljiffry, et al., Evidence-Based Approach to Cholangiocarcinoma: A Systematic Review of the Current Literature, American College of Surgeons, 2009, pp. 134-147, vol. 208 No. 1.
Noori Akhtar-Danesh, et al., Treatment Modality and Trends in Survival for Gallbladder Cancer: a Population-Based Study, Journal of Gastrointestinal Cancer, 2021, pp. 256-262, vol. 52.
Apinya Jusakul, et al., Whole-Genome and Epigenomic Landscapes of Etiologically Distinct Subtypes of Cholangiocarcinoma, Cancer Discovery, 2017, pp. 1116-1135.
Rocio I.R. Maciasa, et al., The search for novel diagnostic and prognostic biomarkers in cholangiocarcinoma, BBA—Molecular Basis of Disease, 2018, pp. 1468-1477, vol. 1864.
Sumera Rizvi, et al., Cholangiocarcinoma-evolving concepts and therapeutic strategies, Nature Reviews Clinical Oncology, 2017, pp. 1-17.
Phunchai Charatcharoenwitthaya, et al., Utility of Serum Tumor Markers, Imaging, and Biliary Cytology for Detecting Cholangiocarcinoma in Primary Sclerosing Cholangitis, Hepatobiliary Malignancies, 2008, pp. 1106-1117, vol. 48 No. 4.
Kwondo Kim, et al., Identification of potential biomarkers for diagnosis of pancreatic and biliary tract cancers by sequencing of serum microRNAs, BMC Medical Genomics, 2019, pp. 1-11, vol. 12 No. 62.
Ana Florencia Vega-Benedetti, et al., Clustered protocadherins methylation alterations in cancer, Clinical Epigenetics, 2019, pp. 1-20, vol. 11 No. 100.

(Continued)

*Primary Examiner* — Sarae L Bausch
(74) *Attorney, Agent, or Firm* — Bayramoglu Law Offices LLC

(57) ABSTRACT

A method—implemented in vitro—for the diagnosis and/or prognosis, preferably in the early stage, of benign or malignant neoplasms of the biliary tract is provided. The method is based on the selection and measurement of the hypermethylation levels of a genetic locus in samples of nucleic acids extracted from tumor tissues and from minimally and/or non-invasive matrices from patients with BTC and a relative comparison of the hypermethylation levels with levels of the same marker in non-tumor samples. A kit for carrying out the above method is also provided.

9 Claims, 5 Drawing Sheets

Specification includes a Sequence Listing.

(56) References Cited

OTHER PUBLICATIONS

Kathleen Saavedra, et al., Epigenetic alterations in preneoplastic and neoplastic lesions of the cervix, Clinical Epigenetics, 2012, pp. 1-7, vol. 4 No. 13.
Yanxin Luo, et al., Differences in DNA Methylation Signatures Reveal Multiple Pathways of Progression From Adenoma to Colorectal Cancer, Gastroenterology, 2014, pp. 418-429, vol. 147 No. 2.
Bodil Oster, et al., Identification and validation of highly frequent CpG island hypermethylation in colorectal adenomas and carcinomas, International Journal of Cancer, 2011, pp. 2855-2866, vol. 129.
Antonio Fadda, et al., Colorectal cancer early methylation alterations affect the crosstalk between cell and surrounding environment, tracing a biomarker signature specific for this tumor, International Journal of Cancer, 2018, pp. 1-14.
Bodo Klump, et al., Promoter Methylation of INK4a/ARF as Detected in Bile—Significance for the Differential Diagnosis in Biliary Disease, Clinical Cancer Research, 2003, pp. 1773-1778, vol. 9.
Baek-Hui Kim, et al., CpG island hypermethylation and repetitive DNA hypomethylation in premalignant lesion of extrahepatic cholangiocarcinoma, Virchows Arch, 2009, pp. 343-351, vol. 455.
Akira Ishikawa, et al., Frequent p16ink4a Inactivation Is an Early and Frequent Event of Intraductal Papillary Neoplasm of the Liver Arising in Hepatolithiasis, Human Pathology, 2007, pp. 1505-1514, vol. 35 No. 2.
Eleonora Loi, et al., Methylation alteration of SHANK1 as a predictive, diagnostic and prognostic biomarker for chronic lymphocytic leukemia, Oncotarget, 2019, pp. 4987-5002, vol. 10 No. 48.
Rattaya Amornpisutt, et al., DNA methylation level of OPCML and SFRP1: a potential diagnostic biomarker of cholangiocarcinoma, Tumor Biol., 2015, pp. 4973-4978,vol. 36.
V. Branchi, et al., Promoter hypermethylation of SHOX2 and SEPT9 is a potential biomarker for minimally invasive diagnosis in adenocarcinomas of the biliary tract, Clinical Epigenetics, 2016, pp. 1-11, vol. 8 No. 133.
Kim Andresen, et al., Novel target genes and a valid biomarker panel identified for cholangiocarcinoma, Epigenetics, 2012, pp. 1249-1257, vol. 7 No. 11.
Farshad Farshidfar, et al., Integrative Genomic Analysis of Cholangiocarcinoma Identifies Distinct IDH-Mutant Molecular Profiles, Cell Reports, 2017, pp. 2780-2794, vol. 18.
Timothy Robert Church, et al., Prospective evaluation of methylated SEPT9 in plasma for detection of asymptomatic colorectal cancer, Gut, 2014, pp. 317-325, vol. 63.
Ludovic Barault, et al., Discovery of methylated circulating DNA biomarkers for comprehensive non-invasive monitoring of treatment response in metastatic colorectal cancer, Gut, 2018, pp. 1995-2005, vol. 67.
Yassen Assenov, et al., Comprehensive analysis of DNA methylation data with Rrnbeads, Nature Methods, 2014, pp. 1-8.
Ana Florencia Vega-Benedetti, et al., Colorectal Cancer Early Detection in Stool Samples Tracing CpG Islands Methylation Alterations Affecting Gene Expression, International Journal of Moleculer Sciences, 2020, pp. 1-18, vol. 21 No. 12.
Sheng-Fang Su, et al., A Panel of Three Markers Hyper- and Hypomethylated in Urine Sediments Accurately Predicts Bladder Cancer Recurrence, Clinical Cancer Research, 2014, pp. 1978-1989, vol. 20 No. 7.
Mark Abramowicz, et al., A Stool DNA Test (Cologuard) for Colorectal Cancer Screening, The Medical Letter on Drugs and Therapeutics, p. 2566, vol. 312 No. 23.
Kim E.M. Van Kessel, et al., Validation of a DNA methylation-mutation urine assay to select patients with hematuria for cystoscopy, The Journal of Urology, 2016, pp. 1-32.
Heidi D. Pharo, et al., A robust internal control for high-precision DNA methylation analyses by droplet digital PCR, Clinical Epigenetics, 2018, vol. 10 No. 24.
Timothy J. Triche Jr, et al., Low-level processing of Illumina Infinium DNA Methylation BeadArrays, Nucleic Acids Research, 2013, pp. 1-11, vol. 41 No. 7.
Andrew E. Teschendorff, et al., A beta-mixture quantile normalization method for correcting probe design bias in Illumina Infinium 450 k DNA methylation data, Bioinformatics, 2013, pp. 189-196, vol. 29 No. 2.
Gordon K. Smyth, Linear Models and Empirical Bayes Methods for Assessing Differential Expression in Microarray Experiments, Statistical Applications in Genetics and Molecular Biology, 2004, pp. 1-25, vol. 3 No. 1.
Kepher Makambi, Weighted inverse chi-square method for correlated significance tests, Journal of Applied Statistics, 2003, pp. 225-234, vol. 30 No. 2.
Tim Triche, FDb.InfiniumMethylation.hg19, Annotate a group of probes supplied as a GenomicRanges object, getNearest, 2024, pp. 1-6.
Zuguang Gu, et al., Complex heatmaps reveal patterns and correlations in multidimensional genomic data, Bioinformatics, 2016, pp. 2847-2849, vol. 32 No. 18.
Tobias Sing, et al., ROCR: visualizing classifier performance in R, Bioinformatics, 2005, pp. 3940-3941, vol. 21 No. 20.
Antonio Colaprico, et al., TCGAbiolinks: an R/Bioconductor package for integrative analysis of TCGA data, Nucleic Acids Research, 2016, pp. 1.11, vol. 44 No. 8.

* cited by examiner

METHOD FOR THE DIAGNOSIS AND/OR PROGNOSIS OF CANCER OF THE BILIARY TRACT

CROSS REFERENCE TO THE RELATED APPLICATIONS

This application is the national phase entry of International Application No. PCT/IB2022/057191, filed on Aug. 3, 2022, which is based upon and claims priority to Italian Patent Application No. 102021000021455, filed on Aug. 6, 2021, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBPRX039.xml, created on Jan. 26, 2024, and is 12,220 bytes.

TECHNICAL FIELD

The present invention refers to a method—implemented in vitro—for the diagnosis and/or prognosis, even in the early phase, of neoplasms of the biliary tract, based on the measurement of the hypermethylation levels of specific CpG loci.

Furthermore, the present invention also refers to a kit to carry out the above method.

BACKGROUND

Biliary tract cancer (BTC) comprises a group consisting of highly aggressive malignant tumors arising from the epithelium of the biliary tract system, comprising intra and extrahepatic bile ducts, gallbladder and cystic ducts. The clinical classification of BTC is based on the anatomical location of origin: intrahepatic and extrahepatic cholangiocarcinoma (CCA) and gallbladder cancer (GBC).

CCA is the second most common primary liver cancer, with a steadily increasing incidence. The frequency and mortality of BTC vary by geographic region and are related to the distribution of risk factors associated with this cancer [1].

The highest incidence and mortality rates of GBC are recorded in Latin America, particularly in the Andean area, while Southeastern Asia has the highest rates for CCA, mainly associated with parasitic infections [2]. In Western countries, major risk factors for CCA include biliary tract diseases such as benign stenosis, primary sclerosing cholangitis (PSC), hepatolithiasis, and choledochus cysts, and these tumors show low but gradually increasing incidence rates [3]. In particular, patients with PSC have a 400 times greater risk of developing CCA than the general population [4]. Early diagnosis of CCA in these patients is difficult as the associated inflammatory process leads to biliary stenosis that mimic the early stages of tumor development [5].

Due to the initial asymptomatic course and clinical manifestations only in the advanced stages, BTCs are usually diagnosed when the tumor is locally advanced or metastatic, therefore unresectable. Furthermore, even when the disease is localized and surgical resection is performed, the risk of recurrence is high and 5-year survival rates remain low, ranging from 15% to 40% for intrahepatic CCA and 25% to 50% for extrahepatic CCA. [6]. The 5-year survival of GBC patients undergoing surgery is much higher and significantly improved reaching up to 70% for stage I and II cancers [7].

A previous history of gallstones, obesity, infections, and ethnicity have been associated with an increased risk of BTC. The incidence of cholangiocarcinomas is increasing in the Western world, with peaks of up to 6/100,000 [8]. On the contrary, in Asian countries and South America the incidence and mortality rates are much higher, probably due to some differences in risk factors for biliary tract cancer between populations on different continents. This difference is especially true for gallbladder cancer. The incidence and mortality rates of GBC, in fact, show a surprising geographical variation worldwide, with rates reaching epidemic levels in some regions of South America, particularly in the Andean area. These large variations can be explained by differences in the prevalence of environmental exposures, in the genetic predisposition to carcinogenesis and in the location of the tumor. Infections could be important in this regard, considering endemic liver fluke infection in South American countries, and chronic hepatitis C inflammation and PSC in Western countries, as key risk factors. The history of infectious diseases such as *Helicobacter pylori* and *Salmonella* could also play an important role.

The current diagnostic strategy for BTC includes a combination of clinical, radiological, biochemical and histological approaches [9]. Endoscopic retrograde cholangiopancreatography (ERCP) combined with brush catheter biliary cytology and cyto-histological analysis of tumor tissue could be performed to confirm a suspected case of BTC [10].

Unfortunately, current diagnostic modalities have shown limited specificity and sensitivity [11,12]. The use of biomarkers is a promising alternative for the detection of BTC and some of them have already been implemented in the clinic, for instance carcinoembryonic antigen (CEA) and carbohydrate antigen 19-9 (CA 19-9). However, high levels of these markers have also been found in benign conditions that affect their specificity [9]. Consequently, accurate diagnosis and especially early diagnosis can prove difficult, highlighting the need for an early diagnosis method for BTC.

DNA methylation alterations are early events during tumorigenesis and can be detected as early as in preneoplastic lesions in many types of tumors [13-17], including CCA [18-20] and even several years before tumor diagnosis [21].

Several biomarkers based on DNA methylation have been proposed to detect BTC in tissue samples. These include OPCML (specificity and sensitivity 100% and 89% respectively) and SFRP1 (specificity and sensitivity 100% and 84% respectively) [22], a two-biomarker panel (SHOX2-SEPT9) (specificity 100% and sensitivity 75%) [23] and a four biomarker panel (CDO1, SFRP1, ZSCAN18 and DCLK1, with 100% specificity and 87% sensitivity) [24]. However, many of these studies have focused on biomarkers that are frequently hypermethylated in other cancers as well, often with a higher incidence than in BTC.

The analysis of the methylation profile of the genome-wide represents a promising strategy for the discovery of new biomarkers specific for BTC. To our knowledge, very few studies have performed a global methylation analysis on BTC samples [8,25]. Importantly, these studies did not aim to identify biomarkers for early BTC detection.

An important advantage for clinical implementation is that methylation alterations can also be detected in circulating free DNA (cfDNA) from different matrices such as blood, urine and faeces [17,26-29].

Furthermore, the ability to detect DNA methylation alterations in liquid biopsies rather than tissue samples would greatly facilitate implementation in the clinical setting, as less invasive procedures are required to obtain these samples.

If not specifically excluded in the detailed description that follows, what is described in this chapter is to be considered as an integral part of the detailed description.

SUMMARY

In light of the above, it is therefore evident the importance of having a method for the determination of neoplasms/tumors of the biliary tract that is non-invasive and that at the same time is characterized by a better sensitivity and specificity than the currently existing methods, ensuring acceptable diagnostic accuracy.

It is therefore an object of the present invention to provide a method that allows the detection of tumors of the biliary tract in the initial stages of the disease and that allows to determine the possible residual presence of cancerous cells, for instance following a surgical treatment—for instance cancer resection—or a therapeutic treatment—for instance chemotherapy and/or radiotherapy—thus allowing the follow-up of the affected and surgically/therapeutically treated subject.

In particular, the object of the present invention is a method for the diagnosis and/or prognosis of tumors of the biliary tract in a subject comprising the following basic steps:
  providing a sample isolated from that subject,
  optionally extracting aliquots of nucleic acids, preferably genomic DNA, from the sample,
  measuring the methylation levels of the genomic DNA in said sample of at least one target sequence chosen in the group consisting of SEQ ID NO: 2 and SEQ ID NO: 4
  comparing said levels with the methylation levels of the corresponding sequences in samples isolated from control subjects and/or with the levels recorded in reference databases obtained with the same experimental methodology and appropriately normalized, wherein an alteration, in terms of increase, of the methylation levels in at least one of said sequences in the sample is indicative of the presence of a biliary tract tumor in the subject.

In one embodiment, the method according to the invention after providing a sample isolated from the subject, comprises the following optional steps:
  extracting the genomic DNA from the sample
  performing a conversion treatment of non-methylated cytosines into uracil on the extracted DNA, preferably with sodium bisulfite
  amplifying with PCR, preferably quantitative, using at least a pair of primers designed to amplify at least one sequence selected from the group consisting of SEQ ID NO: 2 and SEQ ID NO: 4 and complementary to said sequences.

In the method according to the present invention, the step of measuring the methylation levels is performed with a technique suitable for the purpose and known to the skilled in the art, chosen, by way of non-limiting example, in the group consisting of semi-quantitative PCR, quantitative PCR, quantitative PCR specific Methylation (PCR-MS), Next Generation Sequencing, digital PCR, preferably a droplet digital PCR (ddPCR) performed with fluoroform-labeled probes, preferably FAM, TaqMan probes or performed with fluorescent intercalators, non-quantitative PCR followed by sequencing of the single PCR clones either by pyrosequencing or by analysis using High Resolution Melting, methods based on fluorescence, MLPA sauce, SNaPshot and allelic discrimination, Bead array technology, Amplification-refractory mutation system (ARMS), restriction fragment length polymorphism (RFLP), Denaturing Gradient Gel Electrophoresis (DDGE), dot blot, reverse dot blot, Southern blot and other techniques based on hybridization.

In a preferred embodiment, the step of measuring the methylation levels is carried out with ddPCR and comprises the following steps:
  Extracting the genomic DNA from the sample,
  Performing a conversion treatment of non-methylated cytosines into uracil on the extracted DNA, preferably with sodium bisulfite,
  Preparing a reaction mixture comprising said treated DNA, at least a pair of primers designed to amplify at least one sequence selected from the group consisting of SEQ ID NO: 2 and SEQ ID NO: 4 and complementary to said sequences, and at least one probe labeled with a fluorophore capable of pairing with the amplified sequence, preferably chosen from the group consisting of SEQ ID NO: 7 and SEQ ID NO: 10
  generating an emulsion of micro-droplets or droplets by combining the reaction mixture with a PCR oil using an emulsion generator,
  amplifying said DNA with PCR,
  reading the fluorescence generated by the reaction in the appropriate fluorescence reader and quantifying the positive events.

In a preferred embodiment, the primer pairs used in the amplification reactions are selected from the group consisting of SEQ ID NOS: 5 and 6 for the amplification of the genomic portion having SEQ ID NO: 2 and SEQ ID NOS: 8 and 9 for amplification of the genomic portion having SEQ ID NO: 4.

In one embodiment, the sample according to the invention is selected from the group consisting of tissues, preferably a biopsy comprising epithelial tissue of the biliary tract, bile, biliary brush, biological fluid, urine, saliva, faeces, blood and plasma.

In one embodiment, the analysis of the target sequence having SEQ ID NO: 2 is particularly preferred.

This type of method is particularly advantageous for the diagnosis/prognosis of biliary tract tumors and as a follow-up method of the same as it also eliminates the costs associated with the biopsy and the previous surgical technique to obtain the biopsy sample; this advantage is even more evident in consideration of the presence of biliary tract tumors all over the world. This method also eliminates patients' reluctance to undergo bothersome and invasive examinations and techniques, increasing their compliance. The consequence of this is that this method allows for safe and reliable large-scale screening of the population at risk of developing biliary tract cancer. Furthermore, this method represents a valid support in the follow-up of patients in order to identify possible relapses and/or metastases. In support of this, the markers object of the present invention showed a significant correlation between the methylation levels and the survival data of the patients analyzed with patients with higher methylation values presenting a shorter survival, suggesting their usefulness as prognostic markers.

The present invention also relates to a kit for the diagnosis and/or prognosis of biliary tract tumors in a subject comprising at least one pair of primers, said pair consisting of a forward primer and a reverse primer designed to amplify at least one selected target sequence from the group consisting of SEQ ID NO: 2 and SEQ ID NO: 4, essential components for DNA amplification and optionally instructions for use.

In a preferred embodiment the primers are selected from the group consisting of SEQ ID NO: 5, SEQ ID NO: 6, SEQ ID NO: 8, and SEQ ID NO: 9.

In a preferred embodiment, the kit is a kit suitable for use in the ddPCR method and further comprises at least one specific probe, capable of pairing with the amplified sequence, for the analysis of methylation with ddPCR labeled with the FAM fluorophore. The probe is preferably chosen from the group consisting of SEQ ID NO: 7 and SEQ ID NO: 10.

It is also an object of the present invention the use of the kit according to the invention in a method of diagnosis and/or prognosis of biliary tract tumors.

Further objects and advantages of the present invention will become apparent from following detailed description.

From this analysis, 27 significantly altered CpG islands were selected in all three databases and specific for BTC, excluding their alteration in the other gastrointestinal cancers with the highest incidence.

Through the use of an algorithm developed by the inventors applying machine learning techniques, the selection of 2 CpG islands was achieved as possible biomarkers for BTC. By designing specific assays to interrogate certain CpG loci within the two selected islands and using the ultrasensitive method of digital PCR droplet, the sensitivity and specificity of the two assays were tested in a new group consisting of samples, called "tissue exploration group" (18 tumor and 14 non-tumor tissues from the same patients). One of the two assays showed 100% sensitivity and specificity and was then tested in a series of DNA samples extracted from the bile (minimally invasive biological matrix) of 13 BTC patients and 5 controls ("exploratory bile group"), whereon the full sensitivity and specificity of the assay was confirmed.

Figure 2:
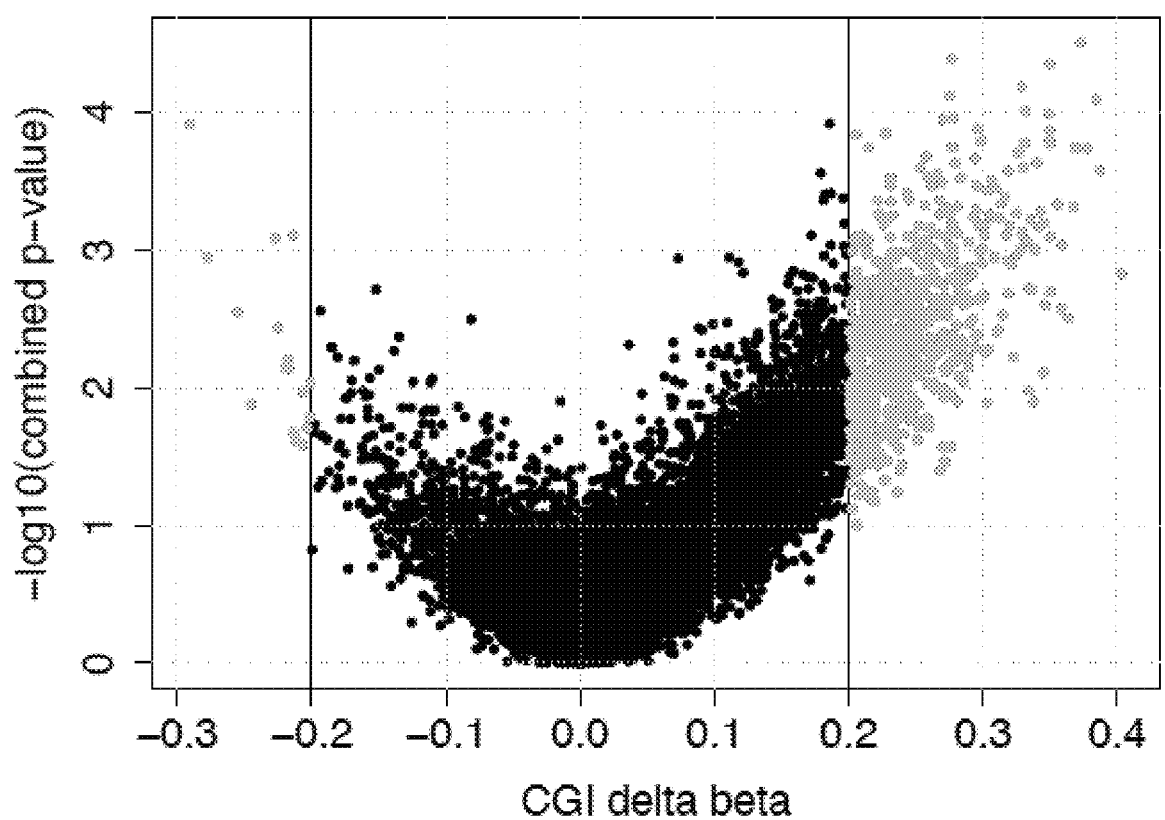

FIG. 2 shows a graph defined as a volcano plot of the distribution of delta beta ($\Delta\beta$) of the CpG islands in the exploratory dataset. On the abscissa axis the $\Delta\beta$, on the ordinate axis the $-\log 10$ of the p-value. The dots indicate hypermethylated CpG islands if $\Delta\beta > 0.2$, hypomethylated islands if $\Delta\beta < -0.2$, considering that R values range from 0 to 1.

Figure 3:
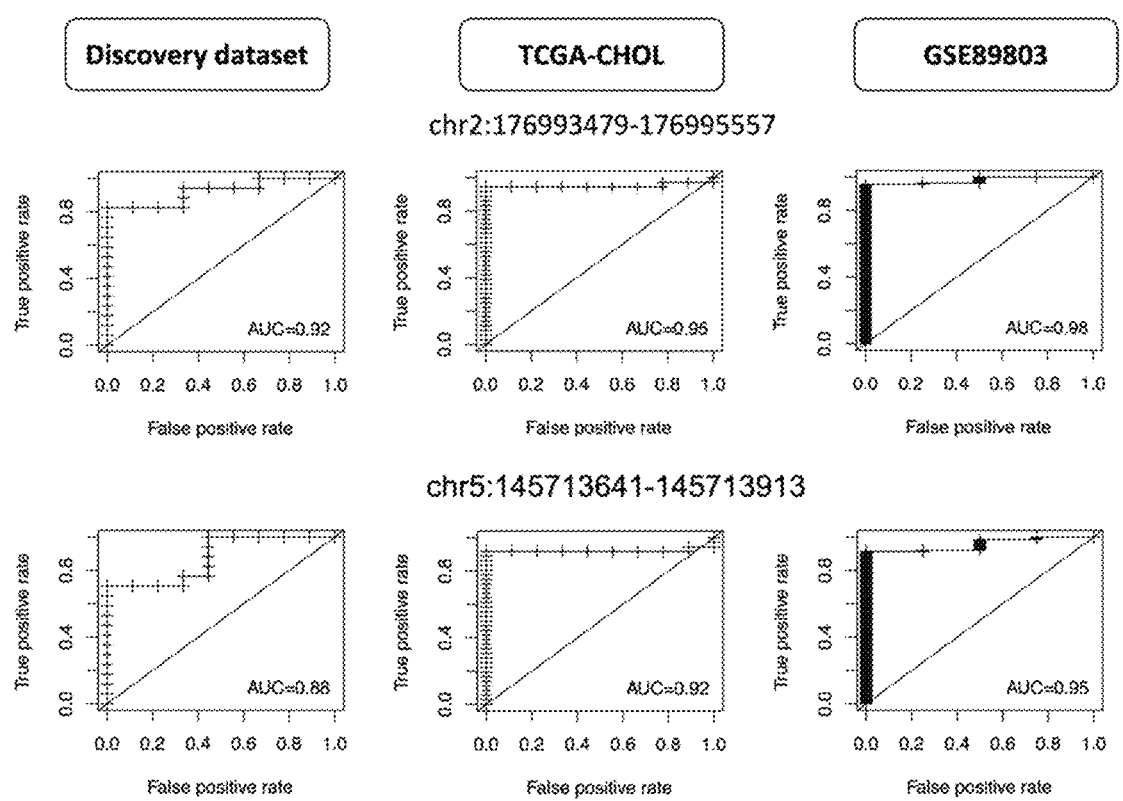

FIG. 3 shows ROC curves illustrating the variation of sensitivity and specificity measures based on the methylation value of a tested marker. The three ROC curves were obtained for the biomarker chr2:176993479-176995557 associated with the HOXD8 gene and for the biomarker chr5:145713641-145713913, in the three datasets initially analyzed for methyloma: Exploratory dataset, TCGA-CHOL, GSE89803.

Figure 4:
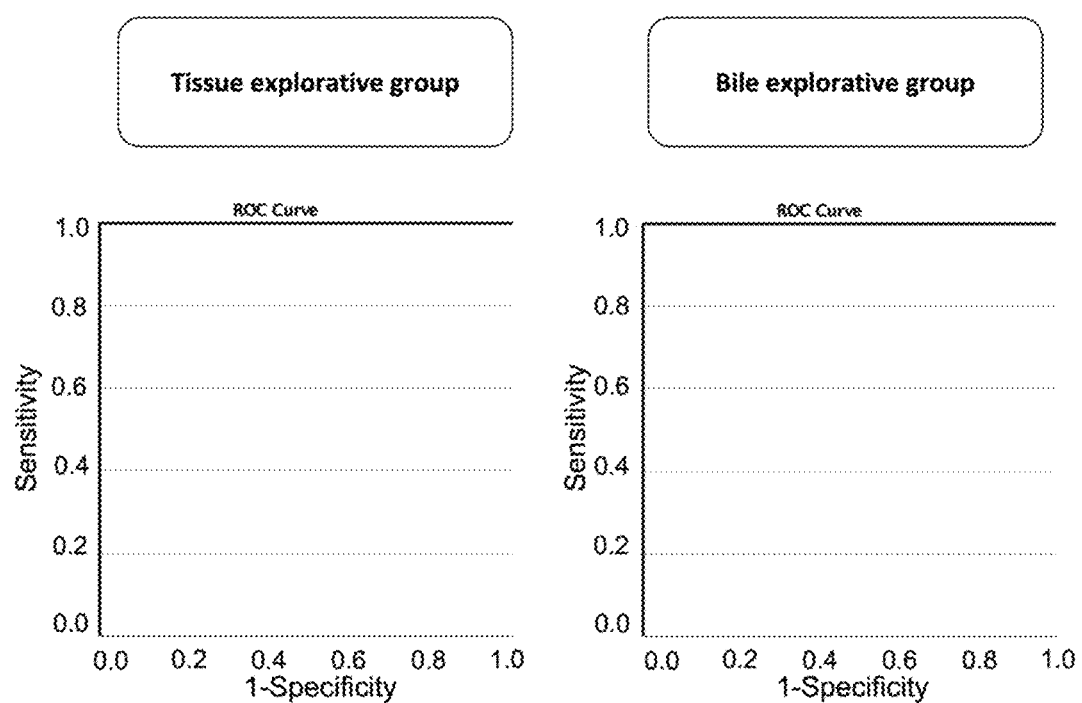

FIG. 4 shows the ROC curve obtained for the biomarker associated with the HOXD8 gene in the so-called "tissue exploration group" and "bile exploration group".

Figure 5:
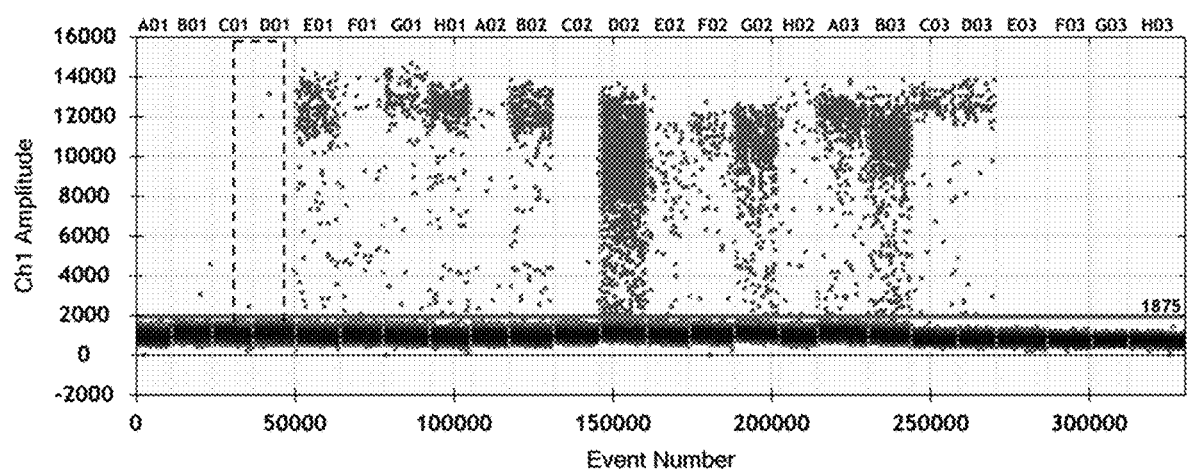

FIG. 5 shows the ddPCR results for the HOXD8 gene-associated marker in bile. The abscissa axis reports the number of droplets (indicated as events) for the tested samples of patients and positive controls. The ordinate axis shows the detected fluorescence amplitude. The dashed box indicates the sample with benign stenosis which showed three positive droplets.

DETAILED DESCRIPTION OF THE EMBODIMENTS

Definitions

In the context of the present invention, "biliary tract neoplasm" (hereinafter also BTC) means any neoplastic formation that develops starting from cholangiocytes (the cells of the biliary tract, located between liver and intestine) and then to affect the internal organ (intrahepatic cholangiocarcinoma), or outside it (extrahepatic cholangiocarcinoma and gallbladder tumor). Specifically, intrahepatic cholangiocarcinomas originate from the small ducts within the liver. The most common extrahepatic cholangiocarcinomas include hilar and perilar carcinomas, most distal carcinomas, and gallbladder carcinomas (GBCs).

Within the scope of the present invention, biliary tract diseases such as benign stenosis, PSC, hepatolithiasis and choledochus cysts are considered among the main risk factors for BTC in Western countries.

In the context of the present invention, "DNA methylation" refers to epigenetic modifications of nucleic acids that alter their accessibility and structure, preferably the structure of chromatin, thus regulating gene expression profiles, which can be influenced by external factors and, as such, they can contribute or be the result of environmental alterations on the phenotype or on the pathophenotype.

In the context of the present invention, the "CpG islands" are regions of the human genome with a high C+G content. These regions are generally about 1 kb long and usually overlap the promoter region of 60-70% of human genes. They are present in repetitions as transposable elements and are involved in the regulation of transcription. Within these regions, most CpG (dinucleotide CpG) pairs are chemically modified with a covalently linked methyl group at position 5 of the cytosine ring. Aberrant methylation of CpGs near transcription initiation sites often leads to alterations in gene expression and dysregulation of signaling pathways involved in cancer.

In the context of the present invention, a "CpG site or locus" refers to a nucleotide having as a nitrogenous base a cytosine, susceptible to the addition of a methyl group by DNA methyl transferase, adjacent to a nucleotide with a guanine to which it binds via a phosphodiester bond.

In the context of the present invention, "hypermethylation" means that the methylation level measured for at least one CpG site of the CpG island object of the present invention is increased in a tested sample (isolated from a subject at risk of biliary tract neoplasm/tumor) compared to a negative sample (a non-tumor biological sample), wherein the negative sample is preferably a DNA sample isolated from healthy subjects not affected by neoplasm/tumor of the biliary tract.

In the context of the present invention, by "specificity" of the marker we mean the ability to discriminate healthy subjects from patients, by "sensitivity" the ability to identify subjects with predisposition to cancer and affected patients, by "accuracy" we mean the quantity of correct disease status attributions.

In the context of the present invention, by "minimally invasive matrices" are meant biological fluids such as bile and biliary brush obtainable by means of a relatively unpleasant and invasive approach commonly used in clinical practice for diagnostic purposes.

DESCRIPTION

The present invention solves and satisfies the needs presented by the prior art by providing a method based on the measurement of methylation levels (hypermethylation) of specific CpG dinucleotides (CpG sites) within CpG islands.

A particularly preferred CpG site is present in a CpG island associated with the HOXD8 gene.

In the context of the present invention, HOXD8 stands for Homeobox D8 or the following synonyms "Homeobox Protein Hox-5.4", "Homeobox Protein Hox-D8", "Homeobox Protein Hox-4E", "Homeo Box D8", "HOX4E", "Homeobox Protein 5.4", "Homeo Box 4E", "Hox-4.5", "HOX5.4", "HOX4".

The CpG sites located in the same CpG island that is altered in methylation, may not reach homogeneous methylation levels or even some loci may not undergo methylation. Therefore, the selection of the CpG loci(us) that ensure the best specificity, sensitivity and accuracy of the test is essential.

The ability to correlate the methylation level of the CpG sites within the aforementioned CpG island ensures the method is more accurate than currently available methods. Furthermore, the method according to the invention allows both the early diagnosis of neoplasms/tumors of the biliary tract, and the follow-up of subjects wherein the tumor has been surgically removed and/or treated with chemo and/or radiotherapy, with specificity and very high sensitivities from a biological sample that may be minimally invasive, such as bile, or even non-invasive, such as from faeces or plasma.

The inventors of the present invention have identified different sequences within CpG islands having differential methylation levels in samples from tumors and normal samples; among these sequences, the inventors have selected a sequence within a CpG island whose methylation level represents a highly discriminating tumor marker for biliary tract cancer. In other words, the marker identified by the inventors allows to discriminate, in a highly specific and selective way, tumor DNA from non-tumor DNA.

As better detailed in the examples below, in order to identify the marker, the inventors performed a genome-wide methylation study of DNA samples extracted from tumor and non-tumor samples of biliary tissue.

All biological samples analyzed were obtained with written and signed informed consent from patients. The study protocol complies with the ethical guidelines of the 1975 Declaration of Helsinki and the studies were carried out with prior approval by the human research committees of the relevant home institutions.

Figure 1:
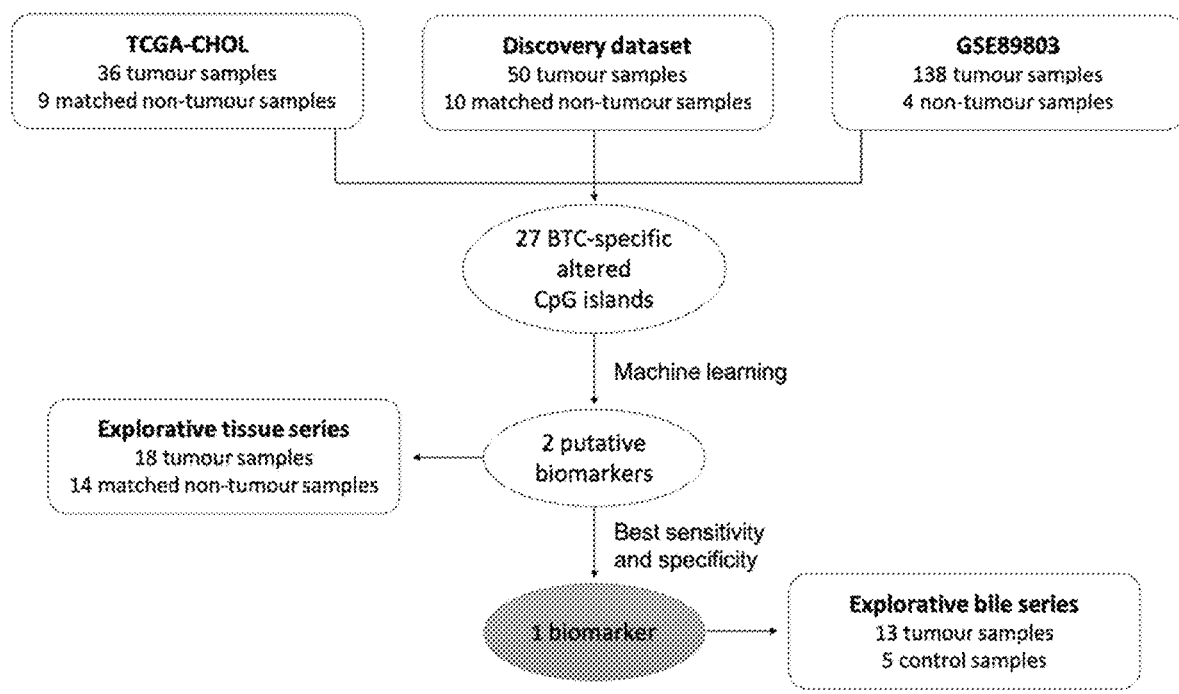
FIG. 1 shows the workflow related to the analyzes carried out for the selection of specific methylation alterations of BTC, starting from an extended genome-wide approach towards one targeted at subject CpG islands. Initially, the methylation pattern extended to the genome-wide was analyzed in a series collected by our group composed of 50 tumor and 10 non-tumor tissues coming from a subgroup consisting of the same patients (exploratory dataset), comparing the results with those of two available online databases, obtained respectively from the study of the methyloma of 36 tumor and 9 non-tumor tissues (TCGA-CHOL) and 138 tumor and 4 non-tumor tissues (GSE89803).

As shown in FIG. 1, in order to select a marker with diagnostic power, an ex vivo profiling approach of genome-wide methylation was initially performed in 50 tissue samples, classified histologically as BTC, of biopsies from tumors having different localization (intrahepatic, extrahepatic and gallbladder) and in 10 matched normal tissue samples. The commercially available platform of high-resolution Illumina microarrays (EPIC® arrays) was used for this first investigation.

After filtering the samples according to the distribution of the R value (it is the ratio between the fluorescence intensity of the methylated probes and the overall intensity given by the sum of the fluorescence intensities of the methylated and unmethylated probes) 26 samples were selected for the analyzes that were of sufficient quality, and in particular 17 tumor samples and 9 samples from non-tumor biopsies.

Differential methylation analysis between tumor and normal samples identified 648 differentially methylated CpG (CGI) islands, including 631 hypermethylated CGI ($\Delta\beta > 0.20$) and 17 hypomethylated CGI ($\Delta\beta < -0.20$) (FIG. 2).

Therefore, only the CGIs that had hypermethylation in tumor tissues were selected, to test the hypothesis that they could be more easily detected even in liquid biopsies, compared to CGIs that become hypomethylated. Furthermore, CGIs showing a $\Delta\beta$ value greater than 0.20 in normal samples (possibly reflecting methylation heterogeneity among non-tumor cells) were excluded, yielding a final set of 171 somatically hypermethylated CGIs.

To increase the solidity of the data obtained and confirm what was obtained experimentally, the inventors also analyzed the methylation data from public databases; in particular, methylation data (obtained with Illumina 450K technology) from The Cancer Genome Atlas (TCGA) (https://portal.gdc.cancer.gov) were used. Within the TCGA data, those relating to cholangiocarcinoma (TCGA-CHOL, including 36 tumors and 9 normal controls) were initially selected. The data were processed following the same pipeline used for the initial dataset. Again, the inventors focused on hypermethylated CGI in tumors.

CGIs showing beta values greater than 0.20 in normal samples were excluded, yielding a total of 998 hypermethylated CGIs. The inventors identified 125 common CGIs between the exploratory dataset and the TCGA-CHOL dataset.

The inventors therefore decided to select only the hypermethylated CGIs in the tumors of interest or to select only the specific alterations of BTC and exclude any hypermethylated CGIs frequent also in other gastrointestinal tumor types. For this purpose the methylation changes of putative biomarkers in other types of gastrointestinal cancer were analyzed using also in this case the data obtained from the TCGA. Out of the 125 previously validated CGIs, all those showing differential methylation ($\Delta\beta > 0.20$) in any of the colon (COAD), rectal (READ) or gastric (STAD) tumors of the TCGA dataset were therefore excluded, obtaining a final set of 30 somatically hypermethylated CGIs, considered specific biomarkers for BTC (Table I).

TABLE I

Methylation values of the 30 CGIs specifically altered in the BTC in the exploratory dataset.

| CGI | Exploratory dataset | | | | | Distance from TSS | Nearest TSS | Distance from gene | Nearest Gene |
|---|---|---|---|---|---|---|---|---|---|
| | Tumor β-value | Normal β-value | Δβ | combined .pval | combined .pval_adj | | | | |
| chr1: 224805408-224805853 | 0.31 | 0.08 | 0.23 | 0.00127996 | 0.199131265 | 1228 | CNIH3 | 0 | CNIH3 |
| chr10: 111216604-111217083 | 0.33 | 0.11 | 0.22 | 0.00302071 | 0.236265951 | 426946 | XPNPEP1 | 407440 | XPNPEP1 |
| chr12: 119212110-119212393 | 0.36 | 0.09 | 0.26 | 0.00298796 | 0.236265951 | 206906 | SRRM4 | 206906 | SRRM4 |
| chr12: 75601081-75601752 | 0.33 | 0.13 | 0.21 | 0.00080747 | 0.195620171 | 1775 | KCNC2 | 0 | KCNC2 |
| chr17: 46670522-46671458 | 0.33 | 0.09 | 0.23 | 0.00151295 | 0.214992741 | 0 | HOXB5 | 0 | HOXB-AS3 |
| chr17: 46796234-46797292 | 0.36 | 0.11 | 0.25 | 0.00118229 | 0.197247818 | 2589 | PRAC1 | 1789 | PRAC1 |
| chr19: 57182887-57183375 | 0.40 | 0.11 | 0.29 | 0.00314887 | 0.23907807 | 0 | ZNF835 | 0 | ZNF835 |
| chr2: 114260095-114261794 | 0.32 | 0.10 | 0.21 | 0.0038351 | 0.253266568 | 3433 | FOXD4L1 | 1367 | FOXD4L1 |
| chr2: 176993479-176995557 | 0.36 | 0.09 | 0.27 | 0.00032765 | 0.192717559 | 0 | HOXD8 | 0 | HOXD8 |
| chr2: 177027617-177028014 | 0.27 | 0.06 | 0.21 | 0.0039372 | 0.25476989 | 790 | HOXD3 | 790 | HOXD3 |
| chr2: 87088816-87089037 | 0.30 | 0.04 | 0.26 | 0.01919055 | 0.42657264 | 0 | ANAPC1P1 | 0 | RMND5A |
| chr20: 61703526-61704022 | 0.29 | 0.07 | 0.22 | 0.00061557 | 0.195620171 | 28621 | HAR1A | 0 | LINC01749 |
| chr21: 27945010-27945646 | 0.29 | 0.08 | 0.21 | 0.00175614 | 0.215260795 | 0 | CYYR1 | 0 | CYYR1 |
| chr3: 181437184-181437478 | 0.38 | 0.14 | 0.24 | 0.00452191 | 0.263195091 | 7471 | SOX2 | 0 | SOX2-OT |
| chr4: 147576109-147576762 | 0.29 | 0.07 | 0.22 | 0.00054074 | 0.195620171 | 16063 | POU4F2 | 12485 | POU4F2 |
| chr5: 113696516-113699195 | 0.30 | 0.07 | 0.22 | 0.0019546 | 0.216448396 | 0 | KCNN2 | 0 | KCNN2 |
| chr5: 140767196-140767695 | 0.33 | 0.12 | 0.21 | 0.01057561 | 0.341639376 | 0 | PCDHGB4 | 0 | PCDHGA1 |
| chr5: 140777442-140777938 | 0.39 | 0.14 | 0.25 | 0.00494213 | 0.263255683 | 0 | PCDHGB5 | 0 | PCDHGA1 |
| chr5: 145713641-145713913 | 0.33 | 0.11 | 0.22 | 0.0020246 | 0.218762425 | 4673 | POU4F3 | 4673 | POU4F3 |
| chr5: 76932317-76933523 | 0.33 | 0.10 | 0.23 | 0.00159148 | 0.214992741 | 998 | OTP | 0 | OTP |
| chr6: 106433984-106434459 | 0.32 | 0.09 | 0.23 | 0.00588658 | 0.272404632 | 99735 | PRDM1 | 99735 | PRDM1 |
| chr6: 150335525-150336278 | 0.29 | 0.07 | 0.22 | 0.00180826 | 0.215260795 | 9244 | RAET1K | 4987 | RAET1L |
| chr6: 27598687-27599146 | 0.35 | 0.12 | 0.23 | 0.00970143 | 0.328901873 | 62667 | LINC01012 | 62667 | LINC01012 |
| chr7: 154001964-154002281 | 0.41 | 0.09 | 0.32 | 0.00067565 | 0.195620171 | 65 | DPP6 | 0 | DPP6 |
| chr7: 27135342-27136736 | 0.28 | 0.07 | 0.21 | 0.00106997 | 0.195620171 | 0 | HOXA1 | 0 | HOXA1 |
| chr7: 27203915-27206462 | 0.37 | 0.12 | 0.25 | 0.00067286 | 0.195620171 | 0 | HOXA9 | 0 | HOXA10-HOXA9 |
| chr7: 27208871-27209616 | 0.31 | 0.11 | 0.20 | 0.0228126 | 0.453729284 | 0 | MIR196B | 0 | HOXA10-HOXA9 |
| chr7: 27283408-27283614 | 0.34 | 0.09 | 0.25 | 0.00272267 | 0.235646056 | 1088 | EVX1 | 0 | EVX1 |
| chr8: 24770908-24772547 | 0.37 | 0.09 | 0.28 | 0.00023564 | 0.19195134 | 0 | NEFM | 0 | NEFM |
| chr9: 36739534-36739782 | 0.42 | 0.07 | 0.35 | 4.55E+09 | 0.18714687 | 83813 | MIR4475 | 61853 | MELK |

The specificity and sensitivity of these 30 biomarkers, altered specifically in the BTC, were evaluated by analyzing the ROC curves (the ROC (Receiver Operating Characteristic) curve is a graph that relates the sensitivity and specificity of a test to varying a threshold value).

The CGIs that showed an area under the curve (AUC) equal to or greater than 0.90 are 11 in the exploratory dataset and 21 in the TCGA-CHOL dataset, of which 7 in common (Table II).

TABLE II

CGI with AUC ≥0.90 in the exploratory dataset and in the TCGA-CHOL dataset

| CGI | AUC Exploratory dataset | AUC TCGA-CHOL dataset |
|---|---|---|
| chr10: 111216604-111217083 | 0.92 | 0.93 |
| chr12: 75601081-75601752 | 0.90 | 1.00 |
| chr17: 46796234-46797292 | 0.93 | 0.94 |
| chr2: 114260095-114261794 | 0.93 | 0.97 |
| chr2: 176993479-176995557 | 0.92 | 0.95 |
| chr5: 113696516-113699195 | 0.92 | 0.93 |
| chr7: 27203915-27206462 | 0.90 | 1.00 |

In order to validate the alterations of the 30 selected CGIs, methylation data were also analyzed from a large dataset downloaded from the NCBI Gene Expression Omnibus (GEO) Portal (https://www.ncbi.nlm.nih.gov/geo/), with access number GSE89803, comprising 138 BTC tumors and four normal control tissues, from patients belonging to different ethnic groups. Methylation alterations ($\Delta\beta>0.20$) were confirmed for 27 out of the 30 CGIs. It is to be noted that two out of three CGIs whose alteration was not confirmed in this dataset showed high methylation values in both the tumor and normal samples. To select the most significant biomarkers, in terms of sensitivity and specificity, a bioinformatics approach based on machine learning processes was applied on the 27 CGIs identified with the first screening.

The approach, developed with proprietary software, led to an extremely compact model that selected out of the initial 27 only two biomarkers (CGI mapping on chr2:176993479-176995557 and chr5:145713641-145713913), reaching AUC=0.972, sensitivity=0.944 and specificity=1.00 on the TCGA dataset, and AUC=0.982, sensitivity=0.964 and specificity=1.00, on the GSE89803 dataset.

This approach selected 2 presumed biomarkers from the panel of 27 initial sequences (FIG. 1).

As a further step towards the future implementation of these biomarkers in clinical contexts, the application of specific DNA methylation assays by digital PCR in tissue and bile samples has been finalized, leading to the definition of a biomarker for BTC completely sensitive and specific (FIGS. 1, 3, 4). Specifically, 50 tissue and bile samples were used, out of which 45 were newly collected and 5 previously analyzed by Illumina EPIC array.

Droplet digital PCR (ddPCR) is an extremely sensitive, robust, fast and relatively inexpensive technique, ideal for absolute quantification of DNA molecules of interest with a low copy number.

The key aspect of ddPCR is the partitioning of the sample and reagents into thousands of droplets, formed in an oil-water emulsion, which allow the reaction to be carried out by single droplet, using TaqMan fluorescent probes as in the classic quantitative PCR (qPCR). Thus, the measurement of thousands of independent amplification events in a single sample is obtained, ensuring that there is no competition for the template in the use of reagents and thus allowing even poorly represented templates to be amplified. The protocol provides: the generation of droplets, the amplification reaction in the droplets and the analysis of the droplets.

The two candidate biomarkers mentioned above were tested ex vivo in a series of BTC tissue samples (n=18) and a subset of corresponding normal samples (n=14). The test on the chr2:176993479-176995557 biomarker showed a sensitivity of 100% (n=17/17), a specificity of 100% (n=14/14) and an AUC of 1.00 (FIG. 4), while the sensitivity of the test on chr5:145713641-145713913 biomarker was 76% (n=13/17), specificity was 93% (n=13/14) and AUC was 0.870. The combined panel of two biomarkers resulted in 100% sensitivity (n=17/17) and 93% specificity (n=13/14).

Both markers therefore proved to be effective in discriminating tumor tissues from healthy ones.

Since the test on chr2:176993479-176995557 biomarker showed the highest sensitivity and specificity in tissue samples, the inventors selected this marker for further analyzes on samples derived from liquid biopsies, especially bile. The inventors then examined and evaluated the performance of the chr2:176993479-176995557 biomarker, associated with the HOXD8 gene, in bile samples from patients with BTC, using the ddPCR technique, currently the most sensitive technology available. The bile sample set included 13 samples from patients with BTC and five samples from patients with benign biliary stenosis. Although the number of non-tumor controls was small, the calculated values for sensitivity and specificity were 100% and the AUC was 1.00 (FIG. 4).

Finally, once the performance of the selected marker was confirmed, its specificity was verified, i.e. it was tested whether this biomarker was specific for BTC or could also be detected in subjects at high risk of developing BTC, such as patients with benign stenosis.

The chr2:176993479-176995557 marker gave negative results in bile samples from patients with benign biliary disease, suggesting that the methylation alteration found by the inventors is specific to a state of malignancy (FIG. 5).

The inventors also found, in a sample from a patient with benign stenosis, evidence of fluorescence in three droplets for the marker of interest (FIG. 5, dashed box) and using a threshold for assigning positivity to the test based on best accuracy, rather than the highest sum of sensitivity and specificity, they classified it as positive.

In benign biliary diseases, positivity for this alteration indicates a higher risk of developing BTC than negative samples. Since methylation alterations are early events in carcinogenesis, it would be important to recommend screening for this biomarker in patients with benign biliary diseases. Indeed, the presence of DNA methylation in this assay in these patients can potentially represent an early trigger in the carcinogenesis process. The development of BTC after 10-20 years from a previous benign disease is not uncommon [4]. This possible scenario is also in line with an increasingly growing literature on the use of methylation biomarkers as diagnostics but also as predictors of a neoplasm, managing to predict the development of cancer even ten years before its onset [21].

The inventors therefore demonstrated that the ddPCR analysis approach is one of the preferred alternative techniques for detecting methylation alterations both in tumor tissues and in liquid biopsies such as bile, opening up the possibility of employing this minimally invasive test for early diagnosis of BTC regardless of tumor location.

According to the invention, ex vivo DNA screening based on methylation can be used in combination with the evaluation of other biomarkers, preferably genetic mutations and biochemical parameters, similarly to other strategies described above or already implemented in the clinical setting [30,31] and known to those skilled in the art.

The inventors therefore found and selected two new biomarkers for BTC based on DNA methylation, CGI at position chr2:176993479-176995557 associated with the HOXD8 gene and CGI at position chr5:145713641-145713913. They then prepared a panel for the combined analysis of both markers in tissues deriving from biopsies under examination.

The chr2:176993479-176995557 biomarker, which showed the best performance in tissue samples, also proved to be excellent as a marker even in bile samples, overcoming the previously described problems of the prior art. The marker according to the invention for the diagnosis of BTC can also be analyzed in nucleic acid samples extracted from completely non-invasive matrices, such as faeces, urine, blood.

This selection process made it possible to identify markers that were tested and validated both on various publicly available databases and in independent validation cohorts (FIG. 3), which led to the verification that the identified markers had the following characteristics:
- very high specificity, i.e. the ability to distinguish between tumor and non-tumor tissue
- very high sensitivity
- high selectivity, i.e. the ability to distinguish between BTC tumors (identified) and other tumors (not detected).

The inventors of the present invention have shown that an advantage of the method of the present invention is to determine if a biological sample belongs to a subject affected by BTC as defined above. Furthermore, the inventors have surprisingly found that the two markers have significantly different methylation values in patients with different survival, and that BTC is detected (determined) in the early stages, in subjects at high risk of developing BTC. Therefore, the method according to the invention also has a high prognostic power and can therefore also be used as a tool for the early diagnosis and/or prevention of BTC.

Being a method capable of identifying the tumor from the earliest stages, the method of the present invention is also valid as a prognostic tool and/or for the follow-up of this tumor, preferably following surgery and/or therapeutic treatments, preferably chemotherapy and/or radiotherapy. In another embodiment of the invention, the method may allow to identify the presence of metastases arising from BTC and present in an organ or tissue other than the biliary tract and/or minimal residual disease.

Table III shows the chromosomal coordinates of the CpG islands whose methylation is altered, more preferably the chromosomal coordinates of the specific region, within said CpG islands, having SEQ ID NO: 1, NO: 2, NO: 3 and NO: 4 investigated with the method of the present invention; the name of the gene to which the CpG island is associated; the specificity and sensitivity obtained with the method of the present invention; the Area Under the Curve measured for the island and for the specific region; the nucleotide sequence of both the CpG island and the specific region. The sequences are also provided as SequenceListing in the required format and it is understood that sequences having a high sequence similarity to those reported here are to be considered part of this description.

TABLE III

| | Coordinates | Sequence | Sensitivity | Specificity | AUC | Sequence ID number | Gene ID |
|---|---|---|---|---|---|---|---|
| CpG island | chr2: 176993479-176995557 | CGTAACTTTGAGGCCTGCGCGCTCTCTCGGCAGTAA TTTCACAGGCTTGGCGGAGGAAGTAGGATCGTTAG CATAAGATGGGCCGCCTGCAGCTGCCTGGAACCGG CGCGATCTGAACGCCGGCTGGGAGGCTCCTGGGGG GAACTTGCGGTCGTCTGCCCTCCGCACTCCTCCGGG AACCGCAGCCGGCCCTGGTTCGCTGCGCGCCGGGG CTGAGACCCGGGAGCCGCGTCCTGCCCGAGGAAAT GTCACCCTCCCCAGCGCGAGCCCTTTTTCCCGCCTCA GAACGTTTCTGTCCGCTCTTCTATTTACTCTCTCAGCA AGCCTAATGCCCCCTCCTGCATTCTTCAGCCTCCCCC TGCGCCCAGGGCTGACGTCTATCAAGGGTGAAATG ATGGAAACTATATTCATGGGCATGATTTCCATTAAAT ATCAATTAACCTGAGAGCCTCGGCCAGGCTTGCGGT GCGTCAAGGGTAAATGTACATCTCATTTCCACAGGG CCCGCTCGGCTGGAAAAGAAAGGCTTTGATTTGCTT TGATAACGCCAGGATCTGGGGCCACACTCGCGGCTT TTAATTAAACCACTTCGATATGCCCCAACTCAAATGC ACGGTCCGGTCCGTCAACACCTCTTGTCCACGTTCCC TGGGCTGCACCCGCGTGTCCAGAGCTGCAAAAGCC ACGGGCAACCTCTGCTTTTGCAGCCAGGGGCTCGG GGAGGCAGTCATTTGCTCCGCAGCCTCCTGGGAGTG GCCTCCTTGGCTCCCCCAAGTCTAAGGCTCCGCCGC GGCCCCTCCCTGCCGGCTGCGATCCGCATTCCCGCG GCCCCGGGGCACACGGAGCCCTTGGCAGTGCGTCT TTATGGGCCCCCTTTAAGGCCGGCGGAGGCATCTCG GGCCGGGCGCGGCGCTCCGTCCGTCGGCCGTAGCG ACTGAACTGCGCGCGGATCCCTCCGCGGGGCTCCTC GTCCCCGTCACGCTGACTTTCCGTGCAGTGCTGTGG TGCGAAAATGCCTCGCCGGTGCGCACCGGGTCGGC AGCCTCGGCGGCGGGGGCGAGATTGGCGGGAGGG GGGCGCGGGGGGGCGCGGTAAGAGGTGGCGGC GGGCAGAGGGTGTTTTTTTCTTTTCCCTCCAGAGCC GGGGTTTGTAAACCGAGGCCAGAGTGTCCCCGTGG GCCGAGCGCACTTTTTTCTTGTCCGGGTGCGCTCAG TCACTGGTGCCTGAGAGGAAACAGTGGAGGCAGCG GGGCAGGTCGCCTGGGGCGTCGGCGATTATATTGC | | | 0.921 | 1 | HOXD8 |

TABLE III-continued

| Coordinates | | Sequence | Sensitivity | Specificity | AUC | Sequence ID number | Gene ID |
|---|---|---|---|---|---|---|---|
| | | GGCCGAGCCGGGCGCGCCGGGAAAGGCCGGGAG | | | | | |
| | | GGCGGCGGCGCGCGGGGGCTGGGCGAGGCCCCGC | | | | | |
| | | GACCCGCGAGGGAGGCGGCGCGAAGCCGAGGCGG | | | | | |
| | | CGGGCGCAAGAGCCGGGCATGAGCGCCCAGTAGCT | | | | | |
| | | GAGCGCCCGCGGCTGCCTGGCCTCAGAAGCGACGC | | | | | |
| | | GCGAGCGCGGGGGGCGGCAGCAGCGACGTAGCC | | | | | |
| | | CGGCGGTCCCGGCGGCGAGAGCAGCCGCCCCACAG | | | | | |
| | | GCCCCCGCGGCAGTGCGGCCGAGTCGAGGCTCGCT | | | | | |
| | | CTCTGGCTGCTTAGCGCCGCCCGCCCGCCCGGGGCC | | | | | |
| | | GCCGCCGCTGACGCCCCAATGAGTTCGTACTTCGTG | | | | | |
| | | AACCCGCTGTACTCCAAGTACAAGGCGGCGGCTGC | | | | | |
| | | GGCGGCGGCGGCGGCGGGCGAGGCCATCAATCCC | | | | | |
| | | ACTTACTACGACTGTCACTTCGCGCCCGAGGTCGGC | | | | | |
| | | GGCCGTCACGCCGCCGCCGCAGCAGCCCTGCAGCTC | | | | | |
| | | TATGGCAACAGCGCCGCCGGCTTCCCGCACGCGCCC | | | | | |
| | | CCGCAGGCGCACGCGCACCCGCACCCGTCCCCGCCG | | | | | |
| | | CCCTCCGGGACTGGGTGCGGCGGTAGGGAAGGCCG | | | | | |
| | | GGGCCAGGAGTACTTCCACCCCGGCGGGGCAGCC | | | | | |
| | | CGGCCGCTGCCTACCAGGCCGCCCCCCCTCCTCCTCC | | | | | |
| | | GCATCCTCCGCCTCCGCCGCCACCTCCCCCCTGCGGC | | | | | |
| | | GGGATTGCCTGTCACGGGGAGCCCGCGAAGTTTTA | | | | | |
| | | CGGATACGATAACTTACAGAGACAGCCGATTTTTAC | | | | | |
| | | GACCCAGCAAGAGGCCG | | | | | |
| Refined region | chr2: 176128890- 176128970 | GGGGAACTTGCGGTCGTCTGCCCTCCGCACTCCTCC GGGAACCGCAGCCGGCCCTGGTTCGCTGCGCGCCG GGGCTGAGAC | 100% | 100% | 1.00 | 2 | HOXD8 |
| CpG island | chr5: 145713641- 145713913 | CGTGCCGAGCCCTCACGGACGCTCGGCCTCTGGCCC CTGAATCCCTCTGGGCGTCTCGGATCCTCTGAGCCA CTTTGCAGACAATGCAAGGCAGCGGCCAACAGACG AGTCCCGCAGCAGCTGCGCAGGCGGCGAGTACATG TGAGAAGTTTGTGAAAGGCGACCAGAGAAAGGGA GAGGAAGGCAAGTCAGGCGGCTGCGAACACCTGGC CAGGCAGCCCCGCCAGCTGCCTCGCTGCGCGATGG CATCTTGAGTTCGGGCCCTCCTATCG | | | 0.88 | 3 | |
| Refined region | chr5: 145713679- 145713774 | TGAATCCCTCTGGGCGTCTCGGATCCTCTGAGCCAC TTTGCAGACAATGCAAGGCAGCGGCCAACAGACGA GTCCCGCAGCAGCTGCGCAGGCGGC | 76% | 93% | 0.870 | 4 | |

It is therefore an object of the present invention a method for the in vitro diagnosis of biliary tract tumors in a subject, comprising a step for measuring the methylation level of the genetic loci identified by the inventors in position chr2:176128890-176128970 represented in SEQ ID NO: 2 and chr5:145713679-145713774 represented in SEQ ID NO: 4 and more preferably the locus in position chr2:176128890-176128970 represented in SEQ ID NO: 2, in a biological sample obtained from a subject and a step of comparison of said levels with the levels found in control samples, which allows to establish a threshold beyond which a sample is positive for the test and therefore reveals the presence of a tumor of the biliary tract in the subject under examination.

The sample according to the invention is a sample isolated from a subject, the method object of the present invention is therefore an ex vivo method, i.e. not applied to the subject himself Said sample according to the invention is selected from tissue, biopsy, bile, biliary brush, biological fluid, urine, saliva, faeces, blood and plasma or any biological sample isolated from a subject with suspicion of BTC or at risk of suffering from BTC which includes a source of DNA belonging to that subject, preferably a sample comprising cells of the subject from which it is possible to isolate DNA as described in the invention or free circulating DNA. In a preferred embodiment, the sample is preferably bile or biliary brush, more preferably a blood or faeces sample.

The object of the present invention is a method comprising the following basic steps:

isolating ex vivo a nucleic acid sample from a biological sample obtained from a subject;
  determining the methylation levels of the loci in position chr2:176128890-176128970 represented in SEQ ID NO: 2 and chr5:145713679-145713774 represented in SEQ ID NO: 4 and more preferably of the locus in position chr2:176128890-176128970, in said sample;
  comparing the methylation levels determined in the sample under examination with the levels found in samples obtained from control subjects;
  wherein an alteration, in terms of increased levels of methylation of said locus, with respect to the levels of the corresponding locus in a control sample, is indicative of the presence of a biliary tract tumor in the subject.

As described above, it is possible to compare the levels determined in the sample under examination also with the methylation levels for the corresponding sequences, annotated in the reference database preferably obtained with the same experimental methodology and suitably normalized.

In a preferred embodiment, the method according to the invention comprises the following steps:

iv. isolating ex vivo a biological sample from a subject, preferably the biological sample being selected from: tissue, biopsy, bile, biliary brush, biological fluid, urine, saliva, faeces, blood and plasma;
  v. purifying from said sample a nucleic acid, preferably DNA, more preferably genomic DNA;

vi. analyzing the methylation level in the sample of the loci in position chr2:176128890-176128970 and/or chr5:145713679-145713774 and more preferably of the locus in position chr2:176128890-176128970.

The nucleic acid, preferably DNA, isolation step can be performed with any technique known to the skilled in the art and/or with any kit suitable for the purpose and available on the market; in a preferred embodiment the isolated DNA is high purity DNA; in a preferred embodiment the DNeasy Blood and Tissue (Qiagen) kit is used.

According to a preferred embodiment of the invention, the nucleic acid, preferably the genomic DNA, after being purified, is treated with sodium bisulfite.

Sodium bisulfite converts unmethylated cytosines (C) to uracil (U) and in this way U is read as thymine when, for instance, nucleic acid is subsequently sequenced. However, this conversion does not occur when the C is methylated in position 5. Therefore, in the sequences a methylated C (mC) remains a C after treatment. It is understood that, in the context of the present invention, the use of any commercial method and/or kit known to the skilled in the art which, as an alternative to sodium bisulfite, allows to achieve this purpose is to be considered part of the present invention.

Nucleic acid treatment with sodium bisulfite is performed according to common laboratory procedures or commercially available kits, such as the EZ DNA Methylation Gold™ Kit (Zymo Research).

Preferably, the bisulfite treatment is carried out using an amount of nucleic acid, preferably DNA, which can range from a few nanograms to about 2 micrograms.

The sodium bisulfite treatment method is carried out following the experimental protocol provided by the manufacturer of the commercial EZ DNA Methylation Gold™ kit.

In a preferred embodiment, the nucleic acid, preferably genomic DNA, is amplified before the methylation level assessment step using at least one pair of oligonucleotides (primers), capable of amplifying at least a portion/sequence of the genomic region of interest comprising the CpG loci to be interrogated (chr2:176128890-176128970 and/or chr5:145713679-145713774). Particularly preferred are the primer pairs having SEQ ID NO: 5 and 6 for the chr2 locus: 176128890-176128970 and SEQ ID NO: 8 and 9 for the chr5 locus: 145713679-145713774, as reported in Table IV.

The step of measuring the methylation levels according to the invention can be performed with any technique known to the skilled in the art, particularly preferred are quantitative analysis protocols based on polymerase chain reaction (PCR), preferably a semi-quantitative PCR, more preferably a quantitative PCR or a quantitative Methylation Specific PCR (PCR-MS), more preferably a digital PCR, more preferably a droplet digital PCR, performed with probes labeled with FAM fluorophores, TaqMan probes or alternatively with fluorescent intercalators. By way of non-limiting example, according to the invention it is also possible to use analysis methods based on non-quantitative PCR protocols followed by sequencing of single PCR clones, by pyrosequencing or the PCR products can be analyzed by High Resolution Melting. By way of non-limiting example, other fluorescence-based methods can also be used to detect the methylation value, preferably the use of genotyping techniques such as an MLPA sauce, SNaPshot and allelic discrimination. Bead array technology and Next Generation Sequencing technologies can also be used to assess the methylation profile of subject CpG sites. Among the classical and low-cost molecular biology methods, the Amplification-refractory mutation system (ARMS), restriction fragment length polymorphism (RFLP), Denaturing Gradient Gel Electrophoresis (DDGE), dot blot, reverse dot blot, southern blot and any other hybridization-based technique can also be used. All the above techniques are embodiments that do not exclude the use of any technique aimed at analyzing and/or quantifying the methylation levels of a specific genomic locus.

In a particularly preferred embodiment the analysis and quantification steps are carried out using the Droplet Digital PCR technique comprising the following basic steps carried out in a system suitable for ddPCR, preferably in the QX200™ Droplet Digital™ PCR (BioRad) system:

the preparation of a PCR reaction mix comprising at least a pair of primers for the amplification of the genomic region of interest and a probe that recognizes the amplified, a generation phase of an emulsion of micro-droplets or droplets by combining the reaction mix with a PCR oil carried out by an emulsion generator or Droplet Generator, a PCR amplification step, the reading of the fluorescence generated by the reaction in the appropriate fluorescence reader.

Preferably, the amplification step is carried out using, as described above, at least one pair of oligonucleotides (primers) and a probe for the regions of interest comprising the CpG loci to be interrogated, the particularly preferred primers and probes are shown in Table IV.

TABLE IV

| Marker | Oligo | Sequence (5'→3') | Fluorescence | Quencher | Sequence ID number |
|---|---|---|---|---|---|
| chr2: 176993479- 176995557 | Forward | GGGGAATTTGCGGTCGTT | | | 5 |
| | Reverse | ATCTCAACCCCGACGCG | | | 6 |
| | Probe | TTCGTATTTTTTCGGGAATCG | FAM | MGBNFQ | 7 |
| chr5: 145713641- 145713913 | Forward | TGAATTTTTTTGGGCGTTTCG | | | 8 |
| | Reverse | GCCGCCTACGCAACTACTACG | | | 9 |
| | Probe | AGGTAGCGGTTAATAGACGAGT | FAM | MGBNFQ | 10 |

Alternatively, the amplification step is performed by generating a library of amplicons (i.e. the amplified sequence) specific for the chromosomal locus of interest, i.e. the genomic region to be amplified. For this purpose, platforms known to the expert in the field can be used, by way of non-limiting example the Illumina platform (MiSEQ, NEXT500, MiniSEQ), Thermo-Fisher platform (IonTorrent), Pacific Bioscence, Oxford Nanopore Technologies and GSJunior Platform.

Alternatively, the amplification of genomic DNA after bisulfite treatment can be generic, i.e. a generic amplification of the DNA as a whole (therefore without the specific primers for the gene and/or the CpG island listed above), this in particular when the methylation levels are evaluated/measured using methods that involve the use of chips developed ad hoc for this purpose, such as those reported by the inventors in the example.

As specified above, according to a preferred embodiment of the invention, the CpG island interrogated with the method of the present invention is reported as SEQ ID NO: 1 corresponding to a region associated with the HOXD8 gene extending between the (chromosomal) coordinates 176993480 and 176995557 in chromosome 2 with respect to the hg19 (human genome 19) assembly.

The general and/or specific methylation levels of the CpG island and more preferably of the CpG sites interrogated by the assay described above can be measured/determined by the common techniques known for the purpose. For instance, quantitative digital PCR techniques can be used, more preferably digital droplet PCR wherein the target sequence is quantitatively amplified.

Another alternative method to measure methylation levels involves the use of chips wherein hybridization is performed between the amplified sequences (amplicons) and the probes on the chip. Generally on the chip there are beads that are marked, usually with fluorescent markers, in a different way according to the recognition specificity for methylated (wherein the mC is maintained) or non-methylated (wherein the C is transformed into U) sequences. The measurement of the fluorescence signal from the chip, usually acquired with a scanner and viewable as a heatmap, will take into account the level of methylation in a quantitative manner.

A further method for measuring methylation levels is based on quantitative sequencing, for instance with pyrosequencing techniques.

A further embodiment of the present invention refers to a kit for implementing the method of the present invention, preferably said kit comprising at least one pair of oligonucleotides (primers), said pair of primers being able to amplify at least a portion/sequence of the genomic region of interest and a probe to detect the amplified.

The present invention also relates to a kit for the diagnosis and/or prognosis of biliary tract tumors in a subject comprising at least one pair of primers, said pair consisting of a forward primer and a reverse primer designed to amplify at least one target sequence selected from the group consisting of SEQ ID NO: 2 and SEQ ID NO: 4, essential components for DNA amplification and optionally instructions for use.

In a preferred embodiment the primers are selected from the group consisting of SEQ ID NO: 5, SEQ ID NO: 6, SEQ ID NO: 8, and SEQ ID NO: 9.

In a preferred embodiment, the kit is a kit suitable for use in the ddPCR method and further comprises at least one specific probe, capable of pairing with the amplified sequence, for the analysis of methylation with ddPCR labeled with the FAM fluorophore. The probe is preferably chosen from the group consisting of SEQ ID NO: 7 and SEQ ID NO: 10.

The use of the kit according to the invention in a method of diagnosis and/or prognosis of biliary tract tumors is an object of the present invention too.

The following examples are provided for the sole purpose of illustrating the invention and are not to be considered limiting its scope.

EXAMPLES

A—Collection and Preparation of Samples
Samples for Genome-Wide Methylation Analysis Genome-wide methylation analysis was performed on fifty formalin-fixed, paraffin-embedded (FFPE) tumor tissue samples and ten normal controls from a subset of the same BTC patients (25 male and 25 female, mean age at diagnosis: 70.4±10.9). The samples were obtained from the Oncology Service, Department of Medical Sciences and Public Health of the University of Cagliari (Italy) and IRCCS-Romagnolo Institute for the Study of Tumors (IRST) "Dino Amadori", Meldola, FC (Italy). The samples came from three anatomical locations: extrahepatic bile ducts, intrahepatic bile ducts and gallbladder.

Samples for Digital Droplet PCR

To validate the methylation alterations of the two selected biomarkers, 32 tissue samples (14 paired BTC/normal samples, four BTC samples) were analyzed. Nine out of 18 BTC were gallbladder cancer and nine were cholangiocarcinomas. Five overlapped with those analyzed in the genome-wide study. FFPE samples were collected at the IRCCS-Istituto Romagnolo for the Study of Tumors (IRST) "Dino Amadori", Meldola, FC (Italy) (n=28) and at the Department of Gastroenterology and Hepatology, University Hospital of Navarra, Pamplona (Spain) (n=4).

Methylation of the best biomarker was also evaluated in bile samples. Eighteen bile samples were included, including 13 samples from patients with cholangiocarcinoma (four of which were also tested for tissue samples) and five from patients with benign stenosis. Bile samples were collected during ERCP at the Department of Gastroenterology and Hepatology, University Hospital of Navarra, Pamplona (Spain).

DNA Extraction from Tissue and Bile Samples

DNA was extracted from FFPE tissues using the QIAamp DNA FFPE Tissue Kit (Qiagen) or the QIAamp DNA Kit (Qiagen). DNA was extracted by microdissection of five 10 μm and 20 μm FFPE tissue slides. The DNA concentration was quantified by UV spectrophotometry (NanoDrop Products, Thermo Scientific) and by fluorometric reading (Quant-iT™ PicoGreen® dsDNA Assay Kit).

Circulating DNA (cfDNA) was extracted from 1 mL of bile. Prior to the isolation of cfDNA, the bile was thawed at 4° C. and centrifuged at 14,000 rounds for 10 minutes at 4° C. to ensure removal of impurities in the supernatant. Biliary cfDNA was extracted using the Maxwell RSC ccfDNA Plasma Kit (Promega) according to the manufacturer's instructions. Biliary cfDNA concentrations were determined using a QuantiFluor dsDNA system (Promega) and cfDNA size was analyzed using Agilent 2100 Bioanalyzer (Agilent Technologies).

Conversion with Sodium Bisulfite

The quality of DNA extracted from FFPE samples was assessed prior to bisulfite conversion using the Infinium HD FFPE QC Assay (Illumina). DNA samples that passed this quality control step were treated with bisulfite using the EZ DNA Methylation Gold Kit (Zymo Research). The bisulfite-converted DNA samples underwent a DNArestoration process using the Infinium FFPE DNARestore Kit (Illumina).

Methylation Assay

DNA samples were analyzed using Illumina Infinium Human Methylation EPIC BeadChips (EPIC), which interrogate over 850,000 CpG sites, according to the Illumina Infinium® HD Methylation protocol. Illumina iScan was used to scan and record high resolution images of the emitted fluorescence.

The methylation level for each CpG site was represented as p values based on the fluorescence intensity ratio between methylated and unmethylated probes. Values can range between 0 (unmethylated) and 1 (fully methylated).

DNA Methylation Assay by Droplet Digital PCR

DNA samples were treated with bisulfite using EZ DNA Methylation Gold Kit (Zymo Research).

Primers and probes were designed for the two specific assays of the selected sequences of the CpG islands (chr2: 176993479-176995557 and chr5:145713641-145713913).

The assays were designed on the genomic regions selected based on the methylation information of the CpG sites interrogated by the probes of the methylation array in the CpG islands of interest. In particular, only the regions including CpG sites showing low methylation values in normal samples and high methylation values in tumor samples from the Exploratory Dataset, TCGA-CHOL dataset and GSE89803, were selected. DNA methylation status was analyzed by ddPCR using the QX200™ Droplet Digital™ PCR (BioRad) system as previously described [32]. The ddPCR reaction included primers (900 nM each), probes (250 nM each), 30 ng of tissue-isolated sodium bisulfite-converted DNA or 70 ng of sodium bisulfite-converted DNA from bile and 1×ddPCR Supermix for Probes (BioRad) in a final volume of 22 µl. The 4Plex Control was included in all wells (for sequences for the 4Plex Control see References: [32]). The droplets were generated in the QX200 drop generator (BioRad), with 70 µL of drop generation oil (BioRad) and 20 µL of ddPCR mix and the PCR was performed in a T100 thermal cycler (BioRad) using the cycle recommended by the manufacturer. Finally, the QX200 Droplet Reader (BioRad) was used to read the fluorescence signals.

Genome-Wide Methylation Data Analysis

Raw DNA methylation data (idat file) were analyzed using RnBeads [33], installed in R environment. The analysis is divided into different modules: quality control, preprocessing, tracks and tables, exploratory analysis and differential methylation analysis. Background subtraction was performed using the methylumi package ("enmix.oob" method) [34]. Normalization of type I and type II probes was performed using the BMIQ method [35] implemented in the watermelon package. By default, RnBeads performs differential methylation analysis with hierarchical linear models as implemented in limma package [36]. RnBeads calculates p-values for all CpG sites analyzed. Incorrect p-values at the CpG level are then combined at the level of predefined genomic regions using a generalization of Fisher's method [37]. Aggregated p-values are subject to correction for multiple tests using the Bonferroni-Benjamini false discovery rate (FDR).

In addition to the standard RnBeads output, a custom R script was developed to generate graphs to assess the distribution of each sample's methylation values. Rigorous filtering was applied to exclude 34 samples (33 tumor samples and one normal sample) showing an unusual R value distribution.

The final analysis was carried out on high quality samples, comprising 17 tumor samples and nine normal tissue samples. CGIs were annotated to the closest genes and transcripts using the annotation package FDb.InfiniumMethylation.hg19 [38]. The heatmaps were generated by the R ComplexHeatmap package [39]. Complet linkage and Euclidean distance were used for clustering. Receiver operating characteristic (ROC) curves were generated by the ROCR package [40].

Selection of Biomarkers Using a Machine Learning Approach

We applied an algorithm, based on a machine learning approach, developed by the inventors to select relevant putative biomarkers as indicators or predictors of disease risk.

The application of this approach, using the available databases, led to an extremely compact model that generated a ranking of the best biomarker combinations (based on AUC, sensitivity and specificity).

Analysis of ddPCR Data

QuantaSoft (BioRad) was used for ddPCR data analysis.

In this specific example, the call for the positive drops was performed using the PoDCall algorithm ([32] available at https://ous-research.no/lind/). Normalized DNA methylation levels were calculated by dividing the concentration (copies/µL) of the target by the concentration (copies/µL) of the 4Plex Control and multiplying by 400. Samples with less than three positive droplets for the target were considered negative for the technical essay. Samples with more than three positive droplets were classified as positive or negative based on a threshold calculated as described below.

The ROC curves were generated by using IBM SPSS Statistics. Thresholds for specimen positivity were determined based on their respective ROC curves, using the highest sum of tissue sensitivity and specificity, 2.35 copies/µL for CGI chr2:176993479-176995557 and 1.25 copies/µL for CGI chr5:145713641-145713913 and in bile 0.22 copies/µL for CGI chr2:176993479-176995557.

Sensitivity was calculated as the ratio of positive tumor samples to the total number of tumor samples expressed as a percentage. Specificity was calculated as the ratio of negative non-tumor samples to the total number of non-tumor samples expressed as a percentage.

Publicly Available Datasets

TCGA Dataset

The processed 450K methylation data related to The Cancer Genome Atlas (TCGA), including cholangiocarcinoma (TCGA-CHOL, including 36 tumors and nine normal controls), colon adenocarcinoma (TCGA-COAD, including 313 tumors and 38 normal controls), adenocarcinoma rectal cancer (TCGA-READ, comprising 98 tumors and seven normal controls) and stomach adenocarcinoma (TCGA-STAD, including 395 tumors and two normal controls), were downloaded using the "TCGAbiolinks" Bioconductor package [41]. The data were processed following the same pipeline used for the exploratory dataset.

GEO Dataset

The processed 450K methylation data (after Noob background removal and BMIQ normalization) from a large BTC study (including 138 tumors and four normal controls) were downloaded from the NCBI Gene Expression Omnibus (GEO) portal under access number GSE89803. The data were downloaded using the "GEOquery" Bioconductor package and processed following the same pipeline used for the exploratory dataset and TCGA-CHOL.

Results

Methyloma Alterations in BTC

The genome-wide methylation study was carried out on 50 BTC tissue samples from different locations (intrahepatic, extrahepatic and gallbladder) and ten normal tissue samples from a subset of patients using Illumina EPIC® arrays, the commercially available microarrays with the highest resolution. Following the quality filter based on the distribution of p values, 26 good quality samples were selected for subsequent analyzes, comprising 17 tumor samples and nine normal samples from a subset of patients. The analysis focused on hypermethylated CpG islands in tumor samples, with the rationale that they would be more easily detected in non-invasive matrices than CpG islands that become hypomethylated. To increase the robustness of the identified methylation alterations, CpG islands were selected that also show alterations in a publicly available dataset (TCGA-CHOL), consisting of 36 tumor samples and nine normal tissue samples. To identify specific changes in BTC, altered CpG islands were also excluded in other more frequent types of gastrointestinal cancer. Finally, the methylation alteration of 27 CpG islands was successfully validated in a large dataset (GSE89803) that included 138 tumors and four normal tissue controls from different ethnic groups (FIG. 1).

Selection of Presumed Biomarkers by Means of Machine Learning

To select the most informative biomarkers, in terms of sensitivity and specificity, a Machine Learning approach was applied on the 27 altered CpG islands which identified a panel of two putative biomarkers. We have selected the best combination in terms of very high performance and technical feasibility of the test. The combination of the two biomarkers (CGI on chr2:176993479-176995557 and chr5:145713641-145713913), provided a promising AUC=0.972, sensitivity=0.944 and specificity=1.00 on the TCGA dataset and AUC=0.982, sensitivity=0.964 and specificity=1.00, on the GSE89803 dataset.

Validation of Biomarkers

As a further step towards the future implementation of these biomarkers in the clinical setting, we explored the application of DNA methylation assays by digital PCR on five samples previously analyzed using the Illumina EPIC array and 45 additional tissues (17 tumors, 14 matched controls) and bile (13 tumors and five controls). The results obtained from the analysis of the tissue samples revealed that the chr2:176993479-176995557 assay showed a sensitivity of 100% (n=17/17), a specificity of 100% (n=14/14) and AUC of 1.00 (FIG. 4), while the sensitivity of the chr5:145713641-145713913 test was 76% (n=13/17), the specificity was 93% (n=13/14) and the AUC was 0.870.

Since the chr2:176993479-176995557 assay showed the highest sensitivity and specificity in the tissue samples (FIG. 4) and also in the Exploratory and Validation Datasets (FIG. 3), the bile samples were tested using only this best biomarker. The calculated values for both sensitivity and specificity were 100% and the AUC was 1.00 (FIG. 4).

BIBLIOGRAPHY

[1] Bergquist A, Von Seth E. Epidemiology of cholangiocarcinoma. Best Pract Res Clin Gastroenterol 2015; 29:221-32. https://doi.org/10.1016/j.bpg.2015.02.003.

[2] Sohal D P S, Shrotriya S, Abazeed M, Cruise M, Khorana A. Molecular characteristics of biliary tract cancer. Crit Rev Oncol Hematol 2016; 107:111-8. https://doi.org/10.1016/j.critrevonc.2016.08.013.

[3] Kongpetch S, Jusakul A, Ong C K, Lim W K, Rozen S G, Tan P, et al. Pathogenesis of cholangiocarcinoma: From genetics to signalling pathways. Best Pract Res Clin Gastroenterol 2015; 29:233-44. https://doi.org/10.1016/j.bpg.2015.02.002.

[4] Boonstra K, Weersma R K, van Erpecum K J, Rauws E A, Spanier B W M, Poen A C, et al. Population-based epidemiology, malignancy risk, and outcome of primary sclerosing cholangitis. Hepatology 2013; 58:2045-55. https://doi.org/10.1002/hep.26565.

[5] Rizvi S, Eaton J E, Gores G J. Primary Sclerosing Cholangitis as a Premalignant Biliary Tract Disease: Surveillance and Management. Clin Gastroenterol Hepatol 2015; 13:2152-65. https://doi.org/10.1016/j.cgh.2015.05.035.

[6] Aljiffry M, Abdulelah A, Walsh M, Peltekian K, Alwayn I, Molinari M. Evidence-Based Approach to Cholangiocarcinoma: A Systematic Review of the Current Literature. J Am Coll Surg 2009; 208:134-47. https://doi.org/10.1016/j.jamcollsurg.2008.09.007.

[7] Akhtar-Danesh N, Akhtar-Danseh G G, Seow H, Shakeel S, Finley C. Treatment Modality and Trends in Survival for Gallbladder Cancer: a Population-Based Study. J Gastrointest Cancer 2020:1-7. https://doi.org/10.1007/si2029-020-00397-w.

[8] Jusakul A, Cutcutache I, Yong C H, Lim J Q, Huang M N, Padmanabhan N, et al. Whole-genome and epigenomic landscapes of etiologically distinct subtypes of cholangiocarcinoma. Cancer Discov 2017; 7:1116-35. https://doi.org/10.1158/2159-8290.CD-17-0368.

[9] Macias R I R, Banales J M, Sangro B, Muntane J, Avila M A, Lozano E, et al. The search for novel diagnostic and prognostic biomarkers in cholangiocarcinoma. Biochim Biophys Acta—Mol Basis Dis 2018; 1864:1468-77. https://doi.org/10.1016/j.bbadis.2017.08.002.

[10] Rizvi S, Khan S A, Hallemeier C L, Kelley R K, Gores G J. Cholangiocarcinoma-evolving concepts and therapeutic strategies. Nat Rev Clin Oncol 2018; 15:95-111. https://doi.org/10.1038/nrclinonc.2017.157.

[11] Charatcharoenwitthaya P, Enders F B, Halling K C, Lindor K D. Utility of serum tumor markers, imaging, and biliary cytology for detecting cholangiocarcinoma in primary sclerosing cholangitis. Hepatology 2008; 48:1106-17. https://doi.org/10.1002/hep.22441.

[12] Kim K, Yoo D, Lee H S, Lee K J, Park S B, Kim C, et al. Identification of potential biomarkers for diagnosis of pancreatic and biliary tract cancers by sequencing of serum microRNAs. BMC Med Genomics 2019; 12:1-11. https://doi.org/10.1186/s12920-019-0521-8.

[13] Vega-Benedetti A F, Loi E, Moi L, Blois S, Fadda A, Antonelli M, et al. Clustered protocadherins methylation alterations in cancer. Clin Epigenetics 2019; 11. https://doi.org/10.1186/s13148-019-0695-0.

[14] Saavedra K P, Brebi P M, Roa J C S. Epigenetic alterations in preneoplastic and neoplastic lesions of the cervix. Clin Epigenetics 2012; 4:13. https://doi.org/10.1186/1868-7083-4-13.

[15] Luo Y, Wong C J, Kaz A M, Dzieciatkowski S, Carter K T, Morris S M, et al. Differences in DNA methylation signatures reveal multiple pathways of progression from adenoma to colorectal cancer. Gastroenterology 2014; 147:418-429.e8. https://doi.org/10.1053/j.gastro.2014.04.039.

[16] Øster B, Thorsen K, Lamy P, Wojdacz T K, Hansen L L, Birkenkamp-Demtroder K, et al. Identification and validation of highly frequent CpG island hypermethylation in colorectal adenomas and carcinomas. Int J Cancer 2011; 129:2855-66. https://doi.org/10.1002/ijc.25951.

[17] Fadda A, Gentilini D, Moi L, Barault L, Leoni V P, Sulas P, et al. Colorectal cancer early methylation alterations affect the crosstalk between cell and surrounding environment, tracing a biomarker signature specific for this tumor. Int J Cancer 2018; 143:907-20. https://doi.org/10.1002/ijc.31380.

[18] Klump B, Hsieh C J, Dette S, Holzmann K, Kießlich R, Jung M, et al. Promoter methylation of INK4a/ARF as detected in bile-significance for the differential diagnosis in biliary disease. Clin Cancer Res 2003; 9:1773-8.

[19] Kim B H, Cho N Y, Shin S H, Kwon H J, Jang J J, Kang G H. CpG island hypermethylation and repetitive DNA hypomethylation in premalignant lesion of extrahepatic cholangiocarcinoma. Virchows Arch 2009; 455:343-51. https://doi.org/10.1007/s00428-009-0829-4.

[20] Ishikawa A, Sasaki M, Sato Y, Ohira S, Chen M F, Huang S F, et al. Frequent p16ink4a inactivation is an early and frequent event of intraductal papillary neoplasm of the liver arising in hepatolithiasis. Hum Pathol 2004; 35:1505-14. https://doi.org/10.1016/j.humpath.2004.08.014.

[21] Loi E, Moi L, Fadda A, Satta G, Zucca M, Sanna S, et al. Methylation alteration of SHANK1 as a predictive, diagnostic and prognostic biomarker for chronic lymphocytic leukemia. Oncotarget 2019; 10:4987-5002. https://doi.org/10.18632/oncotarget.27080.

[22] Amornpisutt R, Proungvitaya S, Jearanaikoon P, Limpaiboon T. DNA methylation level of OPCML and SFRP1: a potential diagnostic biomarker of cholangiocarcinoma. Tumor Biol 2015; 36:4973-8. https://doi.org/10.1007/s13277-015-3147-2.

[23] Branchi V, Schaefer P, Semaan A, Kania A, Lingohr P, Kalff J C, et al. Promoter hypermethylation of SHOX2 and SEPT9 is a potential biomarker for minimally invasive diagnosis in adenocarcinomas of the biliary tract. Clin Epigenetics 2016; 8:1-11. https://doi.org/10.1186/s13148-016-0299-x.

[24] Andresen K, Boberg K M, Vedeld H M, Hektoen M, Wadsworth C A, Clausen O P, et al. Novel target genes and a valid biomarker panel identified for cholangiocarcinoma. Epigenetics 2012; 7:1249-57. https://doi.org/10.4161/epi.22191.

[25] Farshidfar F, Zheng S, Gingras M C, Newton Y, Shih J, Robertson A G, et al. Integrative Genomic Analysis of Cholangiocarcinoma Identifies Distinct IDH-Mutant Molecular Profiles. Cell Rep 2017; 18:2780-94. https://doi.org/10.1016/j.celrep.2017.02.033.

[26] Church T R, Wandell M, Lofton-Day C, Mongin S J, Burger M, Payne S R, et al. Prospective evaluation of methylated SEPT9 in plasma for detection of asymptomatic colorectal cancer. Gut 2014; 63:317-25. https://doi.org/10.1136/gutjnl-2012-304149.

[27] Barault L, Amatu A, Siravegna G, Ponzetti A, Moran S, Cassingena A, et al. Discovery of methylated circulating DNA biomarkers for comprehensive non-invasive monitoring of treatment response in metastatic colorectal cancer. Gut 2018; 67:1995-2005. https://doi.org/10.1136/gutjnl-2016-313372.

[28] Vega-Benedetti A F, Loi E, Moi L, Orru S, Ziranu P, Pretta A, et al. Colorectal cancer early detection in faeces samples tracing CPG islands methylation alterations affecting gene expression. Int J Mol Sci 2020; 21:1-16. https://doi.org/10.3390/ijms21124494.

[29] Su S F, De Castro Abreu A L, Chihara Y, Tsai Y, Andreu-Vieyra C, Daneshmand S, et al. A panel of three markers hyper- And hypomethylated in urine sediments accurately predicts bladder cancer recurrence. Clin Cancer Res 2014; 20:1978-89. https://doi.org/10.1158/1078-0432.CCR-13-2637.

[30] Abramowicz M, Zuccotti G, Pflomm J M. A faeces DNA test (Cologuard) for colorectal cancer screening. JAMA—J Am Med Assoc 2014; 312:2566. https://doi.org/10.1001/jama.2014.15746.

[31] van Kessel K E M, Beukers W, Lurkin I, Ziel-van der Made A, van der Keur K A, Boormans J L, et al. Validation of a DNA Methylation-Mutation Urine Assay to Select Patients with Hematuria for Cystoscopy. J Urol 2017; 197:590-5. https://doi.org/10.1016/j.juro.2016.09.118.

[32] Pharo H D, Andresen K, Berg K C G, Lothe R A, Jeanmougin M, Lind G E. A robust internal control for high-precision DNA methylation analyses by droplet digital PCR. Clin Epigenetics 2018; 10:24. https://doi.org/10.1186/s13148-018-0456-5.

[33] Assenov Y, Müller F, Lutsik P, Walter J, Lengauer T, Bock C. Comprehensive analysis of DNA methylation data with RnBeads. Nat Methods 2014; 11:1138-40. https://doi.org/10.1038/nmeth.3115.

[34] Triche T J, Weisenberger D J, Van Den Berg D, Laird P W, Siegmund K D. Low-level processing of Illumina Infinium DNA Methylation BeadArrays. Nucleic Acids Res 2013; 41:1-11. https://doi.org/10.1093/nar/gkt090.

[35] Teschendorff A E, Marabita F, Lechner M, Bartlett T, Tegner J, Gomez-Cabrero D, et al. A beta-mixture quantile normalization method for correcting probe design bias in Illumina Infinium 450 k DNA methylation data. Bioinformatics 2013; 29:189-96. https://doi.org/10.1093/bioinformatics/bts680.

[36] Smyth G K. Linear models and empirical bayes methods for assessing differential expression in microarray experiments. Stat Appl Genet Mol Biol 2004; 3. https://doi.org/10.2202/1544-6115.1027.

[37] Makambi K H. Weighted inverse chi-square method for correlated significance tests. J Appl Stat 2003; 30:225-34. https://doi.org/10.1080/0266476022000023767.

[38] Triche J T. FDb.InfiniumMethylation.hg19: Annotation package for Illumina Infinium DNA methylation probes. R Packag Version 220 2014.

[39] Gu Z, Eils R, Schlesner M. Complex heatmaps reveal patterns and correlations in multidimensional genomic data. Bioinformatics 2016; 32:2847-9. https://doi.org/10.1093/bioinformatics/btw313.

[40] Sing T, Sander O, Beerenwinkel N, Lengauer T. ROCR: Visualizing classifier performance in R. Bioinformatics 2005; 21:3940-1. https://doi.org/10.1093/bioinformatics/bti623.

[41] Colaprico A, Silva T C, Olsen C, Garofano L, Cava C, Garolini D, et al. TCGAbiolinks: An R/Bioconductor package for integrative analysis of TCGA data. Nucleic Acids Res 2016; 44:e71. https://doi.org/10.1093/nar/gkv1507.

What is claimed is:

1. A method for detecting the presence of biliary tract tumor in a subject comprising
providing a sample isolated from the subject,
measuring the methylation levels of genomic DNA in the sample of at least one target sequence selected from the group consisting of SEQ ID NO: 2 and SEQ ID NO: 4 by extracting the genomic DNA from the sample;
performing a conversion treatment of non-methylated cytosines into uracil on the extracted DNA with sodium bisulfite; and
amplifying by PCR using primer pairs designed to amplify at least one sequence selected from the group consisting of SEQ ID NO: 2 and SEQ ID NO: 4, wherein the primer pairs are selected from the group consisting of SEQ ID NO: 5 and 6 for the amplification of SEQ ID NO: 2 and SEQ ID NO: 8 and 9 for the amplification of SEQ ID NO: 4; and
comparing the levels with the methylation levels of the corresponding sequences in samples isolated from a control subject and/or levels noted in a reference database, wherein an increase of methylation levels in at least one of SEQ ID NO: 2 or SEQ ID NO: 4 in the sample compared to control subject or reference database is indicative of the presence of a biliary tract tumor in the subject.

2. The method according to claim 1, wherein the step of measuring the methylation levels is performed with a technique chosen from the group consisting of semi-quantitative PCR, quantitative PCR, quantitative specific Methylation PCR (PCR-MS), digital PCR, digital droplet PCR (ddPCR) with fluorescent or fluorescent intercalating probes, non-quantitative PCR followed by sequencing of the single PCR clones.

3. The method according to claim 1, wherein the step of amplifying with PCR is carried out with ddPCR and comprises the following steps:
preparing a reaction mixture comprising said treated DNA, the primer pairs designed to amplify at least one sequence selected from the group consisting of SEQ ID NO: 2 and SEQ ID NO: 4 and complementary to said sequences, and at least one probe labeled with a fluorophore capable of pairing with the amplified sequence
generating an emulsion of micro-droplets or droplets by combining the reaction mixture with a PCR oil using an emulsion generator,
amplifying said DNA with PCR, and
reading the fluorescence generated by the reaction in the appropriate fluorescence reader and quantifying the positive events.

4. The method according to claim 3, wherein the probe is selected from the group consisting of SEQ ID NO: 7 and SEQ ID NO: 10.

5. The method according to claim 1, wherein the analyzed target sequence is the sequence having SEQ ID NO: 2.

6. The method according to claim 1, wherein the sample is a biopsy comprising epithelial tissue of the biliary tract.

7. The method according to claim 1, wherein the sample is selected from the group consisting of: tissues, bile, biliary brush, biological fluid, urine, saliva, faeces, blood and plasma.

8. The method according to claim 1, wherein the primer pairs are provided in the form of a kit, the kit comprising: at least one primer pair, said pair consisting of a forward primer and a reverse primer designed to amplify at least one target sequence selected from the group consisting of SEQ ID NO: 2 and SEQ ID NO: 4, essential components for amplification and optionally instructions for use.

9. The method according to claim 2, wherein the target sequence is SEQ ID NO: 2.

* * * * *

SEQUENCE LISTING

```
Sequence total quantity: 10
SEQ ID NO: 1          moltype = DNA  length = 2078
FEATURE               Location/Qualifiers
source                1..2078
                      mol_type = genomic DNA
```

```
                        organism = Homo sapiens
SEQUENCE: 1
cgtaactttg aggcctgcgc gctctctcgg cagtaatttc acaggcttgg cggaggaagt      60
aggatcgtta gcataagatg ggccgcctgc agctgcctgg aaccggcgcg atctgaacgc     120
cggctgggag gctcctgggg ggaacttgcg gtcgtctgcc ctccgcactc ctccgggaac     180
cgcagccggc cctggttcgc tgcgcgccgg ggctgagacc cgggagccgc gtcctgcccg     240
aggaaatgtc accctcccca gcgcgagccc ttttcccgc ctcagaacgt ttctgtccgc      300
tcttctattt actctctcag caagcctaat gcccctcct gcattcttca gcctccccct     360
gcgcccaggg ctgacgtcta tcaagggtga aatgatgaa actatattca tgggcatgat     420
ttccattaaa tatcaattaa cctgagagcc tcggccaggc ttgcggtgcg tcaagggtaa     480
atgtacatct catttccaca gggcccgctc ggctggaaaa gaaaggcttt gatttgcttt     540
gataacgcca ggatctgggg ccacactcgc ggcttttaat taaaccactt cgatatgccc     600
caactcaaat gcacggtccg gtccgtcaac acctcttgtc cacgttccct gggctgcacc     660
cgcgtgtcca gagctgcaaa agccacgggc aactctgct tttgcagcca ggggctcggg     720
gaggcagtca tttgctccgc agcctcctgg gagtggcctc cttggctccc caagtctaa      780
ggctccgccg cggcccctcc ctgccggctg cgatccgcat tcccgcgcc ccggggcaca      840
cggagccctt ggcagtgcgt ctttatgggc cccctttaag gccggcggag gcatctcggg     900
ccggggcggg cgctccgtcc gtcggccgta gcgactgaac tgccgcggca tccctccgcg     960
gggctcctcg tccccgtcac gctgacttc cgtgcagtgc tgtggtgcga aaatgcctcg     1020
ccggtgcgca ccgggtcggc agcctcggcg gcggggcga gattggcggg aggggggcgc     1080
ggggggggcg cggtaagagg tggcggcggg cagagggtgt tttttttctt ttccctccag    1140
agccgggttt tgtaaaccga ggccagagtg tcccccgtgg gccgagcgca ctttttttg      1200
tccgggtgcg ctcagtcact ggtgcctgag aggaaacagt ggaggcagca gggcaggtcg    1260
cctggggcgt cggcgattat attgcggccg agccggggcg cgccgggaaa ggccgggagg    1320
gcggcggcgc gcggggggctg ggcgaggccc cgcgacccgc gagggaggcg gcgcgaagcc    1380
gaggcgggcg gcgcaagagc cgggcatgag cgcccagtag ctgagcgccc gcggctgcct    1440
ggcctcagaa gcgacgcgcg agcgcggggc ggcggcagca gcgacgtagc ccggcggtcc    1500
cggcggcgag agcagccgcc ccacaggccc ccgcggcagt gcggccgagt cgaggctcgc    1560
tctctggctg cttagcgccg cccgcccgcc cggggccgcc gccgctgacg ccccaatgag    1620
ttcgtacttc gtgaaccgc tgtactccaa gtacaaggcg cgctgctggc cggcggcggc     1680
ggcgggcgag gccatcaatc ccacttacta cgactgtcac ttcgcgcccg aggtcggcgg    1740
ccgtcacgcc gccgccgcag cagccctgca gctctatggc aacagcgccc ccggcttccc    1800
gcacgcgccc ccgcaggcgc acgcgcaccc gcacccgtcc ccgccgccct ccgggactgg    1860
gtgcggcggt agggaaggcc ggggccagga gtacttccac ccggcggg gcagcccggc      1920
cgctgcctac caggccgccc ccctcctcc tccgcatcct ccgcctccgc cgccacctcc    1980
ccctgcgc gggattgcct gtcacgggga gcccgcgaag ttttacggat acgataactt     2040
acagagacag ccgattttta cgacccagca agaggccg                           2078

SEQ ID NO: 2                moltype = DNA   length = 81
FEATURE                     Location/Qualifiers
source                      1..81
                            mol_type = genomic DNA
                            organism = Homo sapiens
SEQUENCE: 2
ggggaacttg cggtcgtctg ccctccgcac tcctccggga accgcagccg gccctggttc      60
gctgcgcgcc ggggctgaga c                                                81

SEQ ID NO: 3                moltype = DNA   length = 272
FEATURE                     Location/Qualifiers
source                      1..272
                            mol_type = genomic DNA
                            organism = Homo sapiens
SEQUENCE: 3
cgtgccgagc cctcacggac gctcggcctc tggcccctga atccctctgg gcgtctcgga      60
tcctctgagc cacttgcag acaatgcaag gcagcgacca acagacgagt cccgcagcag     120
ctgcgcaggc ggcgagtaca tgtgagaagt ttgtgaaagg cgaccagaga aagggagagg     180
aaggcaagtc aggcggctgc gaacacctgg ccaggcagcc ccgccagctg cctcgctgcg    240
cgatggcatc ttgagttcgg gccctcctat cg                                  272

SEQ ID NO: 4                moltype = DNA   length = 96
FEATURE                     Location/Qualifiers
source                      1..96
                            mol_type = genomic DNA
                            organism = Homo sapiens
SEQUENCE: 4
tgaatccctc tgggcgtctc ggatcctctg agccactttg cagacaatgc aaggcagcgg      60
ccaacagacg agtcccgcag cagctgcgca ggcggc                                96

SEQ ID NO: 5                moltype = DNA   length = 18
FEATURE                     Location/Qualifiers
source                      1..18
                            mol_type = other DNA
                            organism = synthetic construct
SEQUENCE: 5
ggggaatttg cggtcgtt                                                    18

SEQ ID NO: 6                moltype = DNA   length = 17
FEATURE                     Location/Qualifiers
source                      1..17
```

```
                              mol_type = other DNA
                              organism = synthetic construct
SEQUENCE: 6
atctcaaccc cgacgcg                                                              17

SEQ ID NO: 7          moltype = DNA  length = 21
FEATURE               Location/Qualifiers
source                1..21
                      mol_type = other DNA
                      organism = synthetic construct
SEQUENCE: 7
ttcgtatttt ttcgggaatc g                                                         21

SEQ ID NO: 8          moltype = DNA  length = 21
FEATURE               Location/Qualifiers
source                1..21
                      mol_type = other DNA
                      organism = synthetic construct
SEQUENCE: 8
tgaatttttt tgggcgtttc g                                                         21

SEQ ID NO: 9          moltype = DNA  length = 21
FEATURE               Location/Qualifiers
source                1..21
                      mol_type = other DNA
                      organism = synthetic construct
SEQUENCE: 9
gccgcctacg caactactac g                                                         21

SEQ ID NO: 10         moltype = DNA  length = 22
FEATURE               Location/Qualifiers
source                1..22
                      mol_type = other DNA
                      organism = synthetic construct
SEQUENCE: 10
aggtagcggt taatagacga gt                                                        22
```